(12) United States Patent
Bremer et al.

(10) Patent No.: US 6,475,595 B1
(45) Date of Patent: Nov. 5, 2002

(54) FLUOROCYCLOHEXENE DERIVATIVES, AND LIQUID-CRYSTALLINE MEDIUM

(75) Inventors: Matthias Bremer, Darmstadt; Detlef Pauluth, Ober-Ramstadt; Joachim Krause, Dieburg; Michael Heckmeier, Bensheim; Peer Kirsch, Darmstadt, all of (DE)

(73) Assignee: Merck GmbH, Darmstadt (DE)

( * ) Notice: Subject to any disclaimer, the term of this patent is extended or adjusted under 35 U.S.C. 154(b) by 0 days.

(21) Appl. No.: 09/540,882

(22) Filed: Mar. 31, 2000

(30) Foreign Application Priority Data

Mar. 31, 1999 (DE) .......................... 199 14 684
Mar. 31, 1999 (DE) .......................... 199 14 683
Apr. 29, 1999 (DE) .......................... 199 19 435

(51) Int. Cl.$^7$ ........................ C09K 19/34; C09K 19/30; C07C 25/13
(52) U.S. Cl. ............. 428/111; 252/299.61; 252/299.63; 570/129; 570/130; 570/131; 570/188
(58) Field of Search ....................... 252/299.63, 299.61, 252/299.62; 570/129, 130, 131, 188; 428/1.1

(56) References Cited

U.S. PATENT DOCUMENTS 5,560,863 A * 10/1996 Reiffenrath et al. .... 252/299.01

FOREIGN PATENT DOCUMENTS

JP 4-275244 * 9/1992

OTHER PUBLICATIONS

English abstract of JP 4–275244, 1992*

* cited by examiner

*Primary Examiner*—Shean C. Wu
(74) *Attorney, Agent, or Firm*—Millen, White, Zelano & Branigan, P.C.

(57) ABSTRACT

Fluorocyclohexene derivatives of formula I $$R^1-(A^1-Z^1)_n-A-(Z^2-A^2)_m-Z^3-B-(Z^4-A^3)_p-R^2 \qquad I,$$

in which n, m, p, $R^1$, $R^{2,Z\ 1}$, $Z^2$, $Z^3$, $Z^4$, $A^1$, $A^2$, $A^3$, A and B are as defined herein, are suitable for use in liquid crystal mediums. Also, difluorocyclohexanes of formula III $$R^3-A^*-(Z^6-A^7)_m-Z^7-Q_r-R^7 \qquad III,$$

where $R^3$, $A^*$, $Z^6$, $A^7$, m, $Z^7$, Q, r, and $R^4$ are as defined herein, are suitable for use in liquid crystal mediums.

24 Claims, No Drawings

FLUOROCYCLOHEXENE DERIVATIVES, AND LIQUID-CRYSTALLINE MEDIUM

The invention relates to novel fluorocyclohexene derivatives of the formula I $$R^1—(A^1—Z^1)_n—A—(Z^2—A^2)_m—Z^3—B—(Z^4—A^3)_p—R^2 \quad I$$

in which $R^1$ and $R^2$, independently of one another, are H or an alkyl radical having 1–12 carbon atoms which is unsubstituted or at least monosubstituted by halogen or CN and in which, in addition, one or more $CH_2$ groups may each, independently of one another, be replaced by —O—, —S—, —CO—,

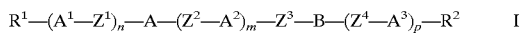

—CO—O—, —O—CO—, —O—CO—O— or —CH=CH— in such a way that heteroatoms are not connected directly, A is 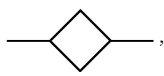

$A^1$, $A^2$ and $A^3$, independently of one another, including if they occur more than once, are
a) a trans-1,4-cyclohexylene radical, in which, in addition, one or more non-adjacent $CH_2$ groups may be replaced by —O— and/or —S—,
b) a 1,4-phenylene radical, in which, in addition, one or two CH groups may be replaced by N,
c) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
d) 1,4-cyclohexenylene,

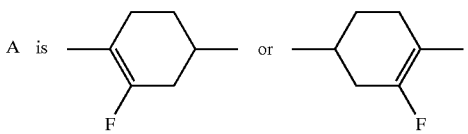

where the radical b) may be monosubstituted or polysubstituted by CN, Cl or F,

B, is a trans-1,4-cyclohexylene radical, in which, in addition, one or more non-adjacent $CH_2$ groups may be replaced by —O— and/or —S—,

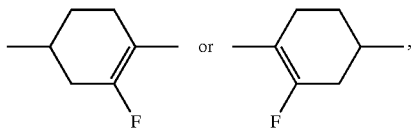

$X^1$ and $X^2$, independently of one another, are H, F, Cl, CN, $CF_3$ or $CHF_2$, $Z^1$, $Z^2$, $Z^3$ and $^4$ are each, independently of one another, —CO—O—, —O—CO—, —$CH_2$O—, —O—, —O—$CH_2$—, —$CH_2CH_2$—, —CH=CH—, —C≡C—,
—$CF_2CF_2$—, —$OCF_2$, —$CF_2O$—, —CH=CF—,
—CF=CH— or a single bond,
and n, m and p, independently of one another, are 0, 1, 2 or 3, where m+n+p is 0, 1, 2 or 3.

The invention also relates to the use of the compounds of the formula I as components of liquid-crystalline media, and to liquid-crystal and electro-optical display elements which contain the liquid-crystalline media according to the invention.

The compounds of the formula I frequently have a highly negative value of the dielectric anisotropy and can be used as components of liquid-crystalline media, in particular for displays based on the principle of the twisted cell, the guest-host effect, the effect of deformation of aligned phases (DAP) or electrically controlled birefringence (ECB) or the effect of dynamic scattering.

DE 4227772 A1 discloses compounds containing fluorocyclohexene rings. However, this document only describes compounds which contain a terminal fluorocyclohexene ring in combination with a perfluoroalkyl radical bonded thereto.

The compounds according to the invention are also covered by a very broad generic claim in DE 4427266 A1, which is directed towards compounds of positive dielectric anisotropy which contain a terminal, optionally fluorinated phenyl radical in combination with a fluorocyclohexene ring. The compounds of the present application are, however, not explicitly mentioned therein.

The substances employed hitherto for this purpose all have certain disadvantages, for example inadequate stability to the action of heat, light or electric fields, or unfavourable elastic and/or dielectric properties.

The invention had the object of finding novel, stable, liquid-crystalline or mesogenic compounds having a broad nematic phase range and negative dielectric anisotropy which are suitable as components of liquid-crystalline media, in particular for TFT and STN displays.

It has now been found that the compounds of the formula I are eminently suitable as components of liquid-crystalline media. They can be used to obtain stable liquid-crystalline media, in particular suitable for TFT or STN displays. The novel compounds are distinguished, in particular, by high thermal stability, which is advantageous for a high "holding ratio", and exhibit favourable clearing point values.

The provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. The addition of compounds of the formula I to liquid-crystalline dielectrics allows the Δε values of such media to be significantly reduced.

The meaning of the formula I covers all isotopes of the chemical elements bound in the compounds of the formula I. In enantiomerically pure or enriched form, the compounds of the formula I are also suitable as chiral dopants and in general for producing chiral mesophases.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media comprising at least one compound of the formula I, and to liquid-crystal display elements, in particular electro-optical display elements, which contain media of this type.

Above and below, n, m, p, $R^1$, $R^2$, A, B, $Z^1$, $Z^2$, $Z^3$, $Z^4$, $A^1$ and $A^2$ and $A^3$ are as defined above, unless expressly stated otherwise. If the radical $A^1$ occurs more than once, it can have the same or different meanings. The same applies to all other groups which occur more than once.

For reasons of simplicity, Cyc below denotes a cyclohexane-1,4-diyl radical, Dio denotes a 1,3-dioxane-2,5-diyl radical, Phe denotes a 1,4-phenylene radical, Dit denotes a 1,3-dithiane-2,5-diyl radical, and Bi denotes a bicyclo[2.2.2]octylene radical, where Cyc and Phe may be unsubstituted or mono- or polysubstituted by halogen or CN, preferably F or CN.

PheXX below denotes

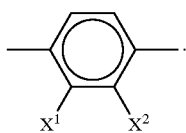

wherein $X^1$ and $X^2$, independently of one another, are H, F, Cl, CN, $CF_3$ or $CHF_2$, preferably at least one of $X^1$ and $X^2$ is F and the other one H or F.

CheF below denotes

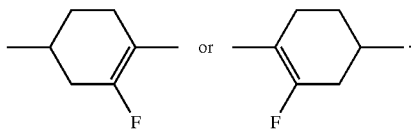

The formula I covers the preferred compounds of the sub-formulae Ia1 to Ia2:

| | |
|---|---|
| $R^1$—Chef—PheXX—$R^2$ | Ia1 |
| $R^1$—CheF—$CH_2CH_2$—PheXX—$R^2$ | Ia2 |

The formula I covers the preferred compounds of the sub-formulae Ib1 to Ib27, which, in addition to the CheF and PheXX groups, contain a further six-membered ring:

| | |
|---|---|
| $R^1$—CheF—Cyc—PheXX—$R^2$ | Ib1 |
| $R^1$—Cyc—$CH_2CH_2$—CheF—PheXX—$R^2$ | Ib2 |
| $R^1$—Cyc—Chef—PheXX—$R^2$ | Ib3 |
| $R^1$—Dio—Chef—PheXX—$R^2$ | Ib4 |
| $R^1$—CheF—$CH_2CH_2$—Cyc—PheXX—$R^2$ | Ib5 |
| $R^1$—Chef—Phe—PheXX—$R^2$ | Ib6 |
| $R^1$—CheF—$CH_2CH_2$—Phe—PheXX—$R^2$ | Ib7 |
| $R^1$—Dio—$CH_2CH_2$—Dio—Chef—PheXX—$R^2$ | Ib8 |
| $R^1$—Phe—Chef—PheXX—$R^2$ | Ib9 |
| $R^1$—CheF—$CH_2CH_2$—Phe—PheXX—$R^2$ | Ib10 |
| $R^1$—Chef—PheXX—Phe—$R^2$ | Ib11 |
| $R^1$—CheF—$CH_2CH_2$—PheXX—Phe—$R^2$ | Ib12 |
| $R^1$—Chef—PheXX—$CH_2CH_2$—Phe—$R^2$ | Ib13 |
| $R^1$—Chef—PheXX—CH=CH—Phe—$R^2$ | Ib14 |
| $R^1$—Chef—PheXX—C≡C—Phe—$R^2$ | Ib15 |
| $R^1$—CheF—$CH_2CH_2$—PheXX—$CH_2CH_2$—Phe—$R^2$ | Ib16 |
| $R^1$—Chef—PheXX—Cyc—$R^2$ | Ib17 |
| $R^1$—CheF—$CH_2CH_2$—PheXX—Cyc—$R^2$ | Ib18 |
| $R^1$—Chef—PheXX—$CH_2CH_2$—Cyc—$R^2$ | Ib19 |
| $R^1$—CheF—$CH_2CH_2$—PheXX—$CH_2CH_2$—Cyc—$R^2$ | Ib20 |
| $R^1$—Chef—PheXX—Dio—$R^2$ | Ib21 |
| $R^1$—CheF—$CH_2CH_2$—PheXX—Dio—$R^2$ | Ib22 |
| $R^1$—Chef—PheXX—CheF—$R^2$ | Ib23 |
| $R^1$—CheF—$CH_2CH_2$—PheXX—CheF—$R^2$ | Ib24 |
| $R^1$—CheF—Chef—PheXX—$R^2$ | Ib25 |
| $R^1$—CheF—$CH_2CH_2$—CheF—PheXX—$R^2$ | Ib26 |
| $R^1$—CheF—CheF—$CH_2CH_2$—PheXX—$R^2$ | Ib27 | furthermore the likewise preferred compounds of the sub-formulae Ic1 to Ic5, which, in addition to the CheF and PheXX groups, contain two six-membered rings:

| | |
|---|---|
| $R^1$—Cyc—Cyc—Chef—PheXX—$R^2$ | Ic1 |
| $R^1$—Cyc—Chef—Phe—PheXX—$R^2$ | Ic2 |
| $R^1$—Dio—Chef—Phe—PheXX—$R^2$ | Ic3 |
| $R^1$—Cyc—CheF—Cyc—PheXX—$R^2$ | Ic4 |
| $R^1$—CheF—Cyc—Cyc—PheXX—$R^2$ | Ic5 | in which $R^1$, Cyc, Dio, CheF, PheXX and $R^2$ are as defined above.

PheXX in the above-mentioned formulae preferably has the following meaning:

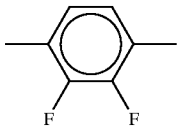

$R^1$ and $R^2$ are preferably, independently of one another, straight-chain alkyl or alkoxy having 1 to 10 carbon atoms or alkenyl or alkenyloxy having 2 to 10 carbon atoms, in particular alkyl or alkoxy having 1 to 7 carbon atoms or alkenyl having 2 to 7 carbon atoms.

In particularly preferred compounds of the formula I, a radical $R^1$ or $R^2$ which is not bonded to an aromatic ring, but instead to a saturated ring, such as Cyc or Dio, is preferably alkyl or alkoxy having 1 to 7 carbon atoms or alkenyl having 2 to 7 carbon atoms, while a radical $R^1$ or $R^2$ which is bonded to an aromatic ring is preferably alkyl or alkoxy having 1 to 7 carbon atoms, in particular alkoxy.

$R^2$ is particularly preferably alkoxy having 1 to 7 carbon atoms.

Particular preference is furthermore given to compounds of the formula I in which $A^1$, $A^2$ and/or $A^3$ have one of the following meanings:

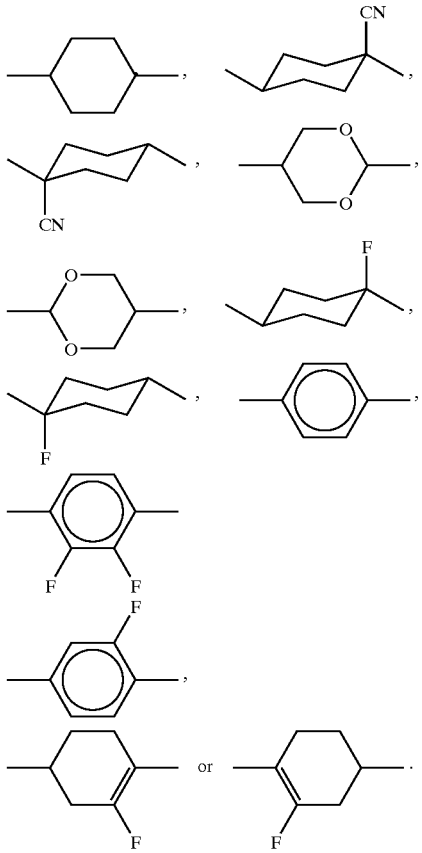

B preferably has the following meaning:

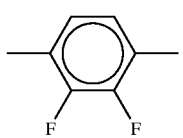

m and n are preferably 0 or 1. m+n is preferably 0 or 1. p is preferably 0.

$Z^1$, $Z^2$, $Z^3$ and $Z^4$ are preferably, independently of one another, —CH$_2$CH$_2$—, —COO—, —OOC— or a single bond, particularly preferably a single bond or —CH$_2$—CH$_2$—.

$X^1$ and $X^2$ are preferably simultaneously F or CN, in particular F.

Particular preference is given to compounds of the formulae IA:

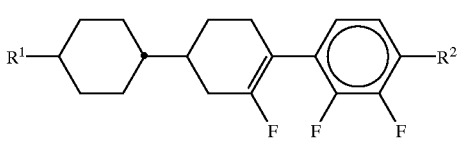

Compounds of the formula I which contain not more than one dioxane ring likewise represent a preferred embodiment of the invention.

Particular preference is furthermore given to the compounds of the formulae I1 to I16 from the following group:

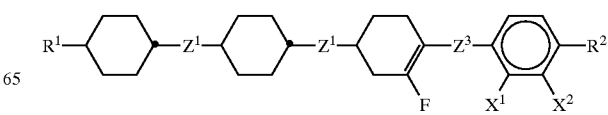

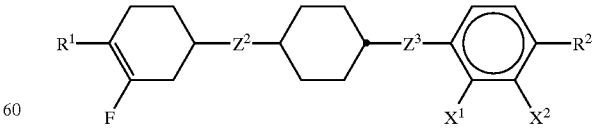

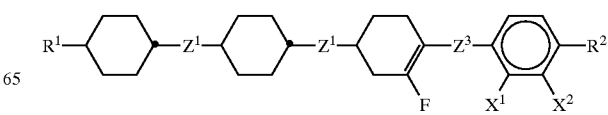

-continued

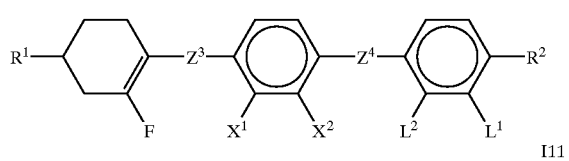
I10

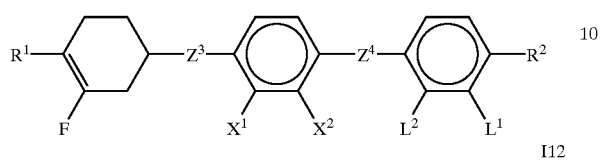
I11

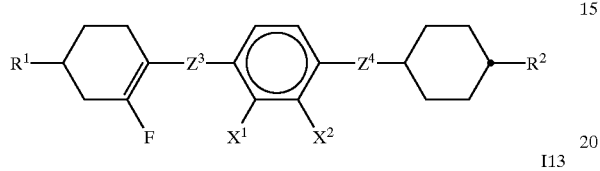
I12

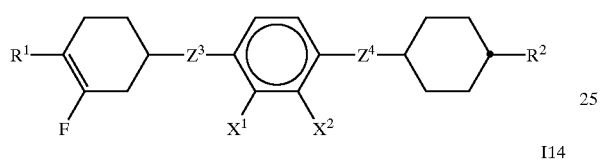
I13

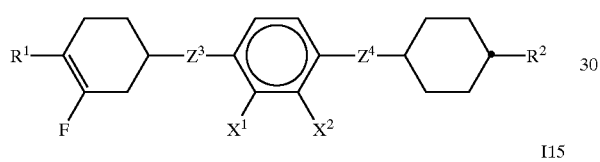
I14

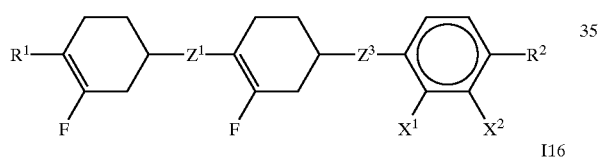
I15

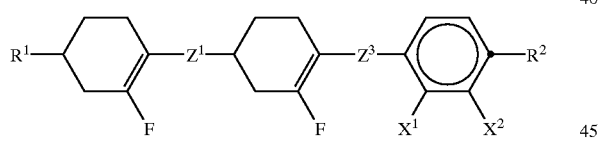
I16 in which $R^1$, $R^2$, $X^1$, $X^2$, $Z^1$, $Z^2$ and $Z^3$ are as defined above, and $L^1$, $L^2$ and $L^3$, independently of one another, are H or F.

Some very particularly preferred smaller groups of compounds of the formula I are those of the sub-formulae I17 to I23:

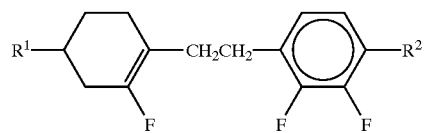
I17

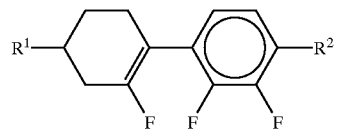
I18

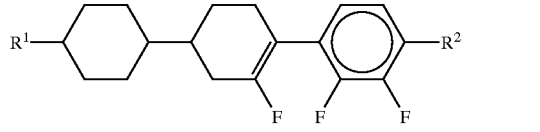
I19

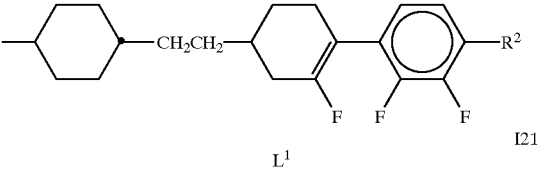
I20

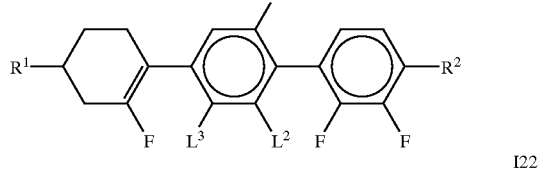
I21

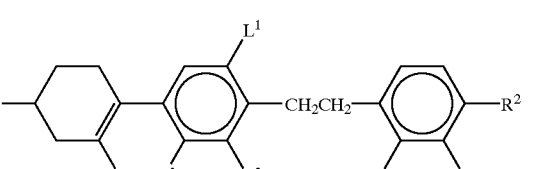
I22

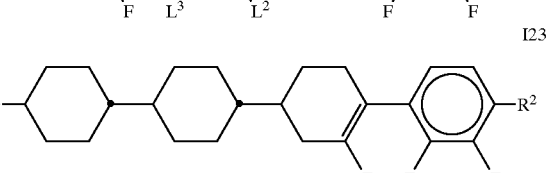
I23

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart) to be precise under reaction conditions which are known and suitable for said reactions.

Use can be made here of variants which are known per se, but are not mentioned here in greater detail.

If desired, the starting materials can also be formed in situ by not isolating them from the reaction mixture, but instead immediately converting them further into the compounds of the formula I.

The compounds of the formula I are preferably obtainable by dehydrofluorination of compounds of the formula II by means of bases:

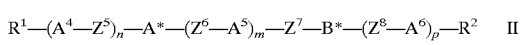
II in which

A* is 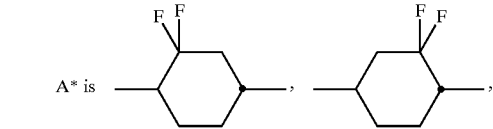

-continued

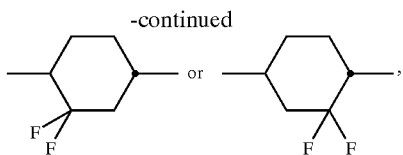

and $A^4$, $A^5$ and $A^6$, independently of one another, including if they occur more than once, are a) a trans-1,4-cyclohexylene radical, in which, in addition, one or more non-adjacent $CH_2$ groups may be replaced by —O— and/or —S—, b) a 1,4-phenylene radical, in which, in addition, one or two CH groups may be replaced by N, c) a radical from the group consisting of 1,4-bicyclo[2.2.2]octylene, piperidine-1,4-diyl, naphthalene-2,6-diyl, deca-hydronaphthalene-2,6-diyl and 1,2,3,4-tetrahydronaphthalene-2,6-diyl, d) 1,4-cyclohexenylene,

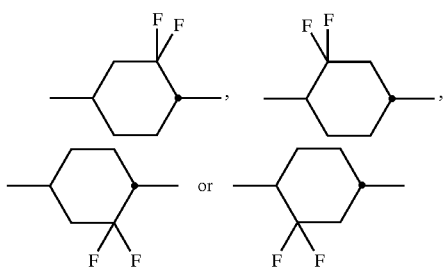

where the radical b) may be monosubstituted or polysubstituted by CN, Cl or F, and the radical a) may be monosubstituted by Cl or F, $Z^5$, $Z^6$, $Z^7$ and $Z^8$ are each, independently of one another, —CO—O—, —O—CO—, —CH$_2$O—, —O—, —O—CH$_2$—, —CH$_2$CH$_2$—, —CH=CH—, —C≡C—, —CF$_2$CF$_2$—, —OCF$_2$—, —CF$_2$O—, —CH$_2$CF$_2$—, —CF$_2$CH$_2$— or a single bond, B*, independently of one another if it occurs more than once, is a trans-1,4-cyclohexylene radical, in which, in addition, one or more non-adjacent $CH_2$ groups may be replaced by —O— and/or —S—,

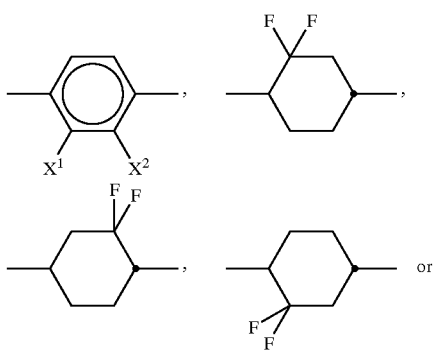

-continued

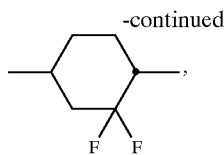

and $R^1$, $R^2$, $X^1$, $X^2$, n, m and p are as defined above.

Of the compounds of the formula II, particular preference is given to the novel difluorocyclohexanes of the subformula III $$R^3—A^*—(Z^6—A^7)_m—Z^7—Qr—R^7 \qquad III$$

in which $R^3$ and $R^4$, independently of one another, are H or an alkyl radical having 1–12 carbon atoms, in which, in addition, one or more $CH_2$ groups may each, independently of one another, be replaced by —O— or —CH=CH— in such a way that heteroatoms are not connected directly,

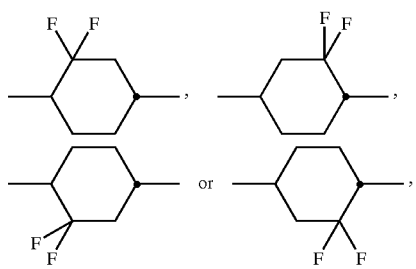

A* is $A^7$, independently of one another if it occurs more than once, is a trans-1,4-cyclohexylene radical, in which, in addition, one or more non-adjacent $CH_2$ groups may be replaced by —O— and/or —S—, where this radical may be monosubstituted by Cl or F,

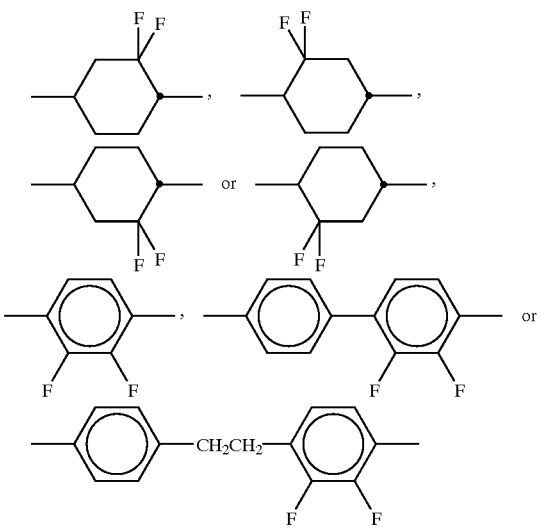

m is 0, 1, 2 or 3,
r is 0 or 1, and
$Z^6$ and $Z^7$ are as defined above, where m+r is 1, 2 or 3, with the proviso that compounds of the formula I in which m is 1, r is 0, $Z^6$ is a single bond, $A^7$ is cyclohexane-1,4-diyl and $R^3$ and $R^4$ are an alkyl group, in which, in addition, one $CH_2$ group may be replaced by —O—, are excluded.

The compounds of the formula III can be used for the preparation of the compounds of the formula I or preferably can themselves be employed as components of liquid-crystalline media.

The compounds of the formula III can be used to obtain stable liquid-crystalline media, in particular suitable for TFT or STN displays. The novel compounds are distinguished, in particular, by high thermal stability, which is advantageous for a high holding ratio, and exhibit favourable clearing point values. Furthermore, they have particularly low optical anisotropy $\Delta n$ and negative dielectric anisotropy $\Delta \epsilon$.

Liquid-crystalline media having very low optical anisotropy values are of particular importance for reflective and transflective applications, i.e. applications in which the respective LCD experiences no or only supporting background illumination. Low $\Delta n$ values are achieved, in particular, using compounds of the formula I which contain no aromatic rings.

The provision of compounds of the formula III very generally considerably broadens the range of liquid-crystalline substances which are suitable, from various applicational points of view, for the preparation of liquid-crystalline mixtures.

JP 5 279 279 discloses similar difluorocyclohexanes. However, this document only describes compounds having two ring members, which are excluded from formula III by the proviso.

Furthermore, difluorocyclohexanes containing three ring members are described in JP 5 058 926. This document relates exclusively to compounds in which the difluorocyclohexane ring is arranged between two rings, but not to the compounds of formula III of the present invention, which contain a terminal difluorocyclohexane ring.

The compounds of the formula III according to the invention are, in addition, covered by the very broad generic claim of DE 4427266, which is directed towards synthesis intermediates. The difluorocyclohexane derivatives of the present application are, however, not explicitly mentioned therein.

The compounds of the formula III have a broad range of applications. Depending on the choice of substituents, these compounds can serve as base materials of which liquid-crystalline media are predominantly composed; however, it is also possible to add compounds of the formula III to liquid-crystalline base materials from other classes of compound in order, for example, to modify the dielectric and/or optical anisotropy of a dielectric of this type and/or to optimize its threshold voltage and/or its viscosity. The addition of compounds of the formula III to liquid-crystalline dielectrics allows the $\Delta n$ values of such media to be significantly reduced.

The meaning of the formula III covers all isotopes of the chemical elements bound in the compounds of the formula III. In enantiomerically pure or enriched form, the compounds of the formula I are also suitable as chiral dopants and in general for producing chiral mesophases.

In the pure state, the compounds of the formula III are colorless and form liquid-crystalline mesophases in a temperature range which is favorably located for electro-optical use. They are stable chemically, thermally and to light.

The invention thus furthermore relates to the compounds of the formula III and to the use of these compounds as components of liquid-crystalline media. The invention furthermore relates to liquid-crystalline media comprising at least one compound of the formula III, and to liquid-crystal display elements, in particular electro-optical display elements, which contain media of this type.

Above and below, $R^1$, $R^2$, $R^3$, $R^4$, $A^*$, $A^4$, $A^5$, $A^6$, $A^7$, $Z^5$, $Z^6$, $Z^{7, Z8}$, Q, r, m, n, p and $B^*$ are as defined above, unless expressly stated otherwise. If the radical $A^7$ occurs more than once, it can have the same or different meanings. The same applies to all other groups which occur more than once.

F-substituted cyclohexane-1,4-diyl below is preferably:

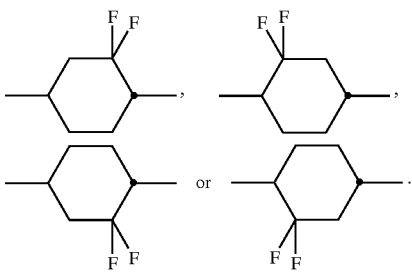

PheFF below is preferably:

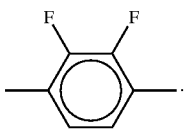

The formula III covers the preferred compounds of the sub-formulae IIIa1 to IIIa6, which, in addition to the group A*, contain one six-membered ring:

| | |
|---|---|
| $R^3$—A*—Cyc—$R^4$ | IIIa1 |
| $R^3$—A*—$CH_2CH_2$—Cyc—$R^4$ | IIIa2 |
| $R^3$—A*—Dio—$R^4$ | IIIa3 |
| $R^3$—A*—$CH_2CH_2$—Dio—$R^4$ | IIIa4 |
| $R^3$—A*—$CH_2CH_2$—PheFF—$R^4$ | IIIa5 |
| $R^3$—A*—PheFF—$R^4$ | IIIa6 | furthermore the likewise preferred compounds of the sub-formulae IIIb1 to IIIb19, which, in addition to the group A*, contain two six-membered rings:

| | |
|---|---|
| R³—A*—Cyc—Cyc—R⁴ | IIIb1 |
| R³—A*—CH₂CH₂—Cyc—Cyc—R⁴ | IIIb2 |
| R³—A*—Dio—Cyc—R⁴ | IIIb3 |
| R³—A*—CH₂CH₂—Dio—Cyc—R⁴ | IIIb4 |
| R³—A*—CYC—CH₂CH₂—Cyc—R⁴ | IIIb5 |
| R³—A*—Dio—CH₂CH₂—Cyc—R⁴ | IIIb6 |
| R³—A*—Cyc—PheFF—R⁴ | IIIb7 |
| R³—A*—CH₂CH₂—CYC—PheFF—R⁴ | IIIb8 |
| R³—A*—Dio—PheFF—R⁴ | IIIb9 |
| R³—A*—CH₂CH₂—Dio—Dio—R⁴ | IIIb10 |
| R³—A*—Phr—PheFF—R⁴ | IIIb11 |
| R³—A*—Phe—CH₂CH₂—PheFF—R⁴ | IIIb12 |
| R³—A*—Dio—CH₂CH₂—PheFF—R⁴ | IIIb13 |
| R³—A*—Cyc—COO—PheFF—R⁴ | IIIb14 |
| R³—A*—Dio—COO—PheFF—R⁴ | IIIb15 |
| R³—A*—CH₂CH₂—Cyc—CH₂CH₂—Cyc—R⁴ | IIIb16 |
| R³—A*—CH₂CH₂—Dio—CH₂CH₂—Cyc—R⁴ | IIIb17 |
| R³—A*—CH₂CH₂—CYC—CH₂CH₂—PheFF—R⁴ | IIIb18 |
| R³—A*—CH₂CH₂—Dio—CH₂CH₂—PheFF—R⁴ | IIIb19 | and the preferred compounds of the sub-formulae IIIc1 to IIIc10, which, in addition to the group A*, contain three six-membered rings:

| | |
|---|---|
| R³—A*—Cyc—Cyc—Cyc—R⁴ | IIIc1 |
| R³—A*—CH₂CH₂—Cyc—Cyc—Cyc—R⁴ | IIIc2 |
| R³—A*—Cyc—Cyc—PheFF—R⁴ | IIIc3 |
| R³—A*—CH₂CH₂—Cyc—Phe—PheFF—R⁴ | IIIc4 |
| R³—A*—Cyc—CH₂CH₂—Cyc—Cyc—R⁴ | IIIc5 |
| R³—A*—Cyc—CH₂CH₂—Cyc—PheFF—R⁴ | IIIc6 |
| R³—A*—Cyc—Dio—Cyc—R⁴ | IIIc7 |
| R³—A*—CH₂CH₂—Cyc—Dio—Cyc—R⁴ | IIIc8 |
| R³—A*—Cyc—CH₂CH₂—Dio—Cyc—R⁴ | IIIc9 |
| R³—A*—Cyc—Dio—CH₂CH₂—Cyc—R⁴ | IIIc10 | in which R³, A*, PheFF, Phe, Cyc, Dio and R⁴ are as defined above.

R³ and R⁴ are preferably, independently of one another, straight-chain alkyl or alkoxy having 1 to 10 carbon atoms; alkenyl or alkenyloxy having 2 to 10 carbon atoms; in particular alkyl or alkoxy having 1 to 7 carbon atoms or alkenyl having 2 to 7 carbon atoms.

Preference is furthermore given to compounds of the formula I in which the radicals R³ and R⁴ or both radicals simultaneously are alkenyl having 2 to 7 carbon atoms.

If the radical R⁴ is bonded to an aromatic ring, it is preferably alkoxy.

Particular preference is furthermore given to compounds of the formula I in which A⁷ has one of the following meanings:

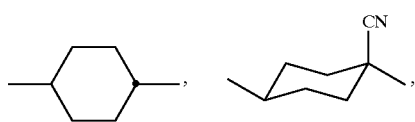
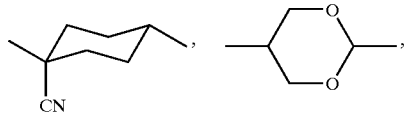
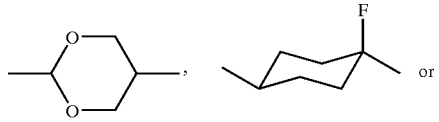
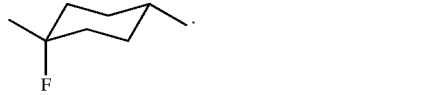

m is preferably 0, 1 or 2, in particular 0 or 1, m+r is preferably 1 or 2,

Z⁶ and Z⁷ are preferably, independently of one another, —CH₂CH₂—, —COO—, —OOC— or a single bond, particularly preferably a single bond or —CH₂—CH₂—.

Particular preference is given to the compounds of the formulae IIIA, IIIB, IIIC, IIID and IIIE:

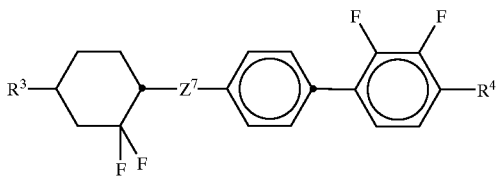

IIIA

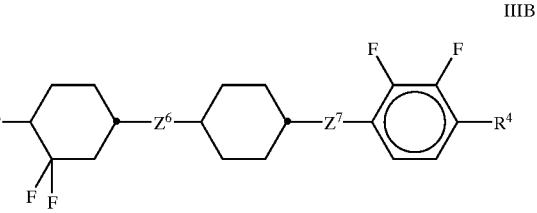

IIIB

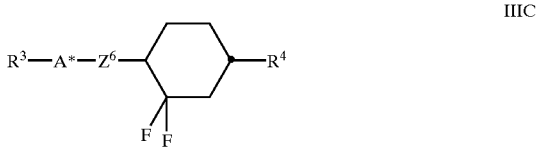

IIIC

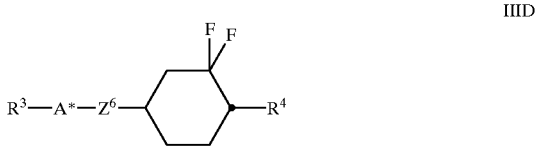

IIID

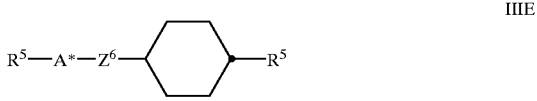

IIIE in which R³, R⁴ and A* are as defined above, Z⁶ and Z⁷ are a single bond or —CH₂CH₂—, in particular a single bond, and R⁵ and R⁶ are as defined for R³ and R⁴, where at least one of the radicals R⁵ and R⁶ is alkenyl.

Compounds of the formula III which contain not more than one dioxane ring likewise represent a preferred embodiment of the invention.

Particular preference is furthermore given to the compounds of the formulae III1 to III11 from the following group:

III1
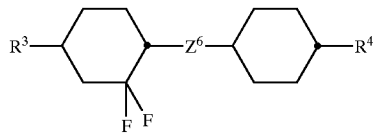

III2
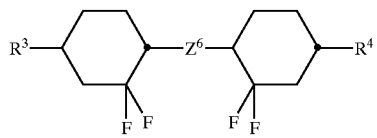

III3
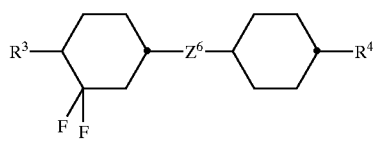

III4
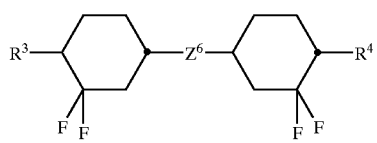

III5
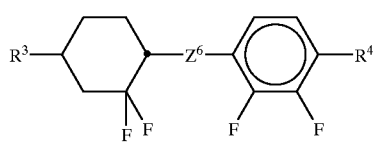

III6
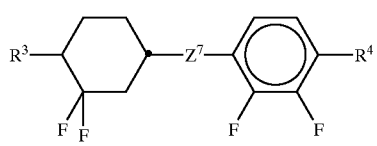

III7
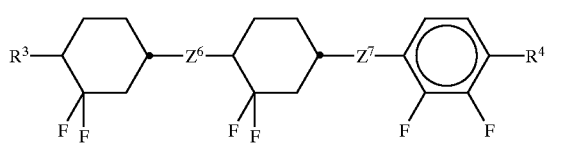

III8
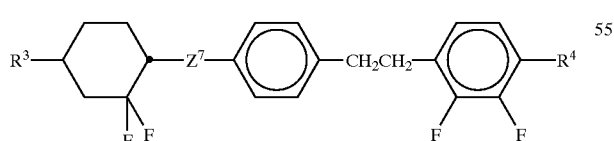

III9
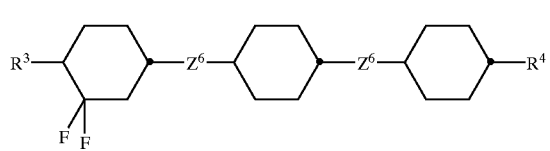

III10
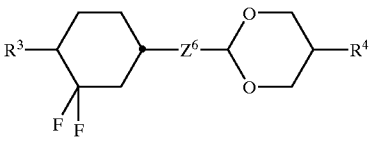

III11
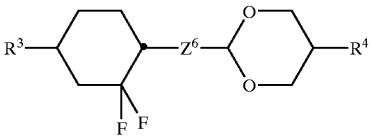

in which $R^3$, $R^4$, $Z^6$ and $Z^7$ are as defined above.

If $R^1$, $R^2$, $R^3$ and/or $R^4$ in the formulae above and below are an alkyl radical, this can be straight-chain or branched. It is preferably straight-chain, has 2, 3, 4, 5, 6, or 7 carbon atoms and accordingly is preferably ethyl, propyl, butyl, pentyl, hexyl or heptyl, furthermore methyl, octyl, nonyl, decyl, undecyl, dodecyl, tridecyl, tetradecyl or pentadecyl.

If $R^1$, $R^2$, $R^3$ and/or $R^4$ are an alkyl radical in which one $CH_2$ group has been replaced by —O—, this can be straight-chain or branched. It is preferably straight-chain and has 1 to 10 carbon atoms. Preferably, the first $CH_2$ group of this alkyl radical is replaced by —O—, so that the radical $R^1$, $R^2$, $R^3$ and/or $R^4$ becomes alkoxy and is preferably methoxy, ethoxy, propoxy, butoxy, pentyloxy, hexyloxy, heptyloxy, octyloxy or nonyloxy.

Furthermore, one $CH_2$ group elsewhere can also be replaced by —O—, so that the radical $R^1$, $R^2$, $R^3$ and/or $R^4$ is preferably straight-chain 2-oxapropyl(=methoxy-methyl), 2-(=ethoxymethyl) or 3-oxabutyl(=2-methoxyethyl), 2-, 3- or 4-oxapentyl, 2-, 3-, 4-or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$, $R^2$, $R^3$ and/or $R^4$ are an alkenyl radical this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, furthermore oct-1-, -2-, -3-, -4-, -5-, -6- -7-enyl, non-1-, -2-, -3-, -4-, -5-, -6-, -7- or -8-enyl, or dec-1-, -2-, -3-, -4-, -5-, -6-, -7-, -8- or -9-enyl.

$R^1$, $R^2$, $R^3$ and/or $R^4$ are particularly preferably an alkenyl radical from the following group:

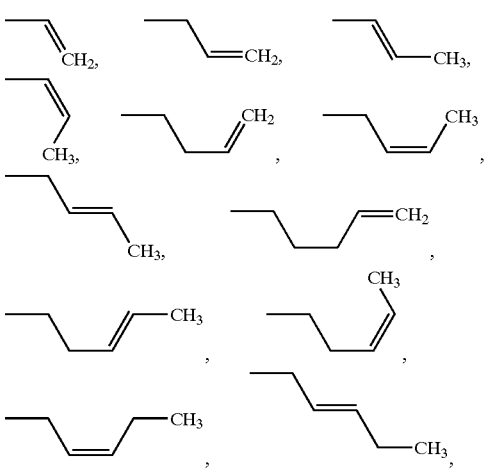

-continued

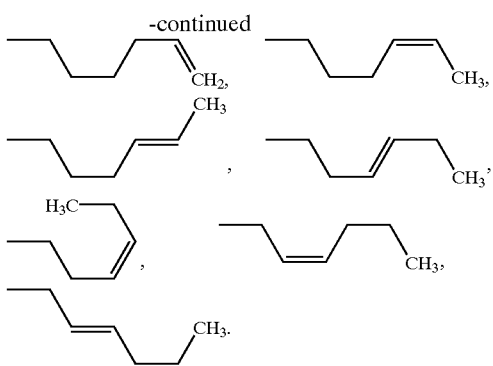

If $R^1$, $R^2$, $R^3$ and/or $R^4$ are an alkenyloxy radical, this can be straight-chain or branched. It is preferably straight-chain and has 2 to 10 carbon atoms. It is particularly preferably a radical from the following group:

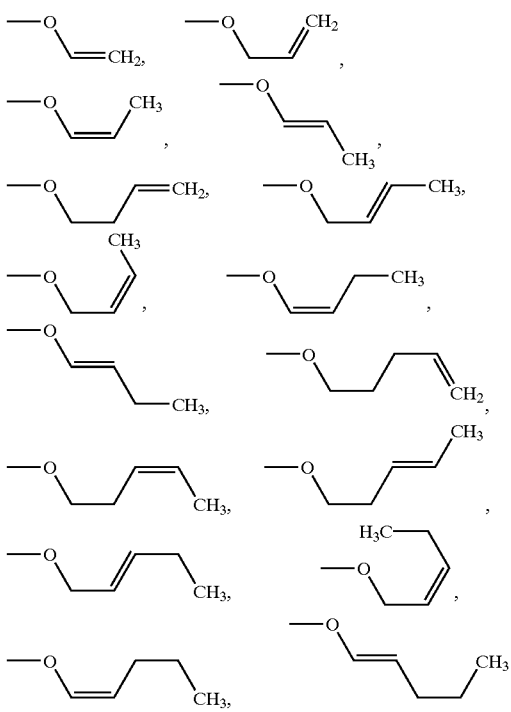

If $R^1$, $R^2$ $R^3$ and/or $R^4$ are an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$, $R^2$, $R^3$ and/or $R^4$ are an alkyl radical which is at least monosubstituted by halogen, this radical is preferably straight-chain. Halogen is preferably F or Cl. In the case of polysubstitution, halogen is preferably F. The resultant radicals also include perfluorinated radicals. In the case of mono-substitution, the fluorine or chlorine substituent can be in any desired position, but is preferably in the ω-position.

Compounds of the formula I containing a branched wing group $R^1$, $R^2$, $R^3$ and/or $R^4$ may occasionally be of importance owing to better solubility in the customary liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$, $R^2$, $R^3$ and/or $R^4$ are isopropyl, 2-butyl(=1-methylpropyl), isobutyl(=2-methylpropyl), 2-methylbutyl, isopentyl(=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

The formulae I, II and III cover the racemates of these compounds and the optical antipodes, and mixtures thereof.

Of these compounds of the formulae I, II and III and the sub-formulae, preference is given to those in which at least one of the radicals present therein has one of the preferred meanings indicated. Some very particularly preferred smaller groups of compounds of the formula III are those of the sub-formulae III12 to III26:

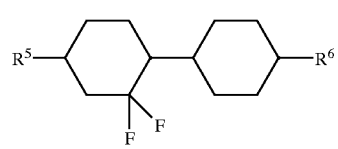

1112

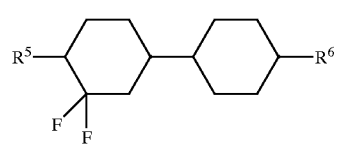

1113

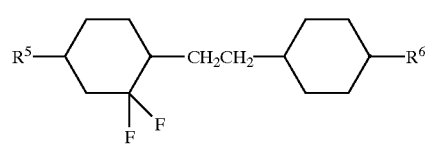

1114

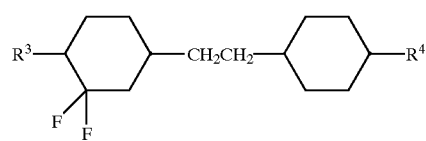

1115

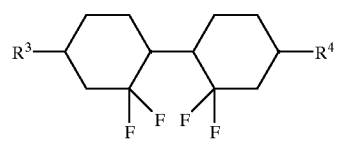

1116

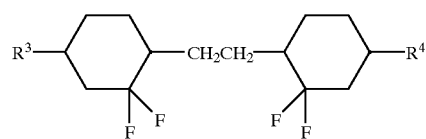

1117

19

-continued

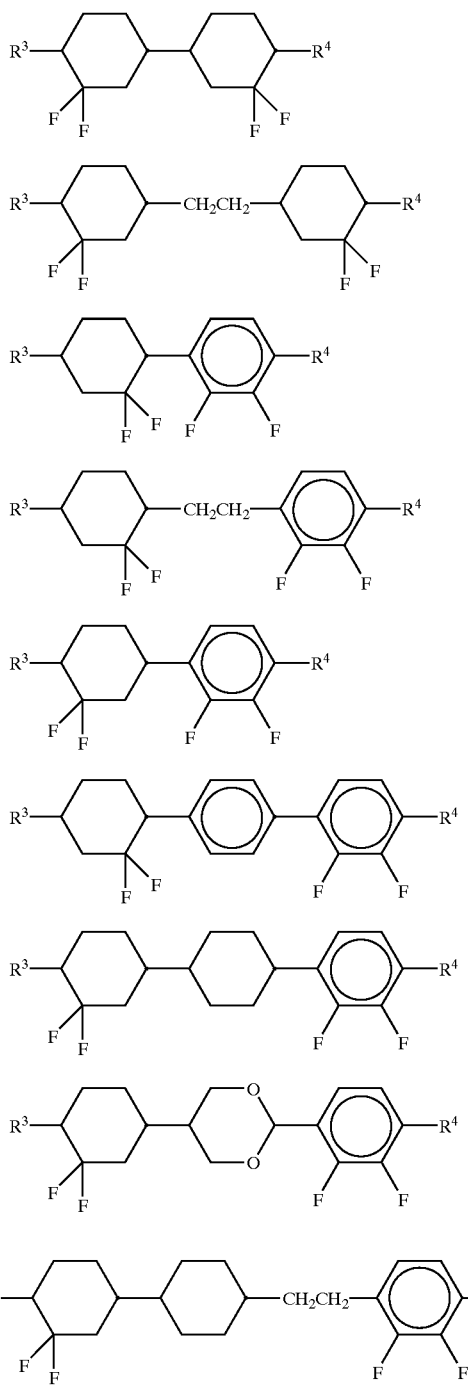

in which $R^3$, $R^4$, $R^5$ and $R^6$ are as defined above.

The compounds of the formulae I, II and III are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can be made here of variants which are known per se, but are not mentioned here in greater detail.

The starting materials can, if desired, also be formed in situ by not isolating them from the reaction mixture, but instead immediately converting them further into the compounds of the formula I, II or III.

The compounds of the formulae II and III which contain an axially fluorinated 1,4-cyclohexanediyl can be synthesized using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis (1973) 779; G. A. Olah, X-Y. Li, Q. Wang, G. K. S. Prakash, Synthesis (1993) 693).

It is likewise possible to obtain the compounds of the formula I by simultaneously eliminating HF from a $Z^5$, $Z^6$, $Z^7$ or $Z^8$ bridge and an A* ring by means of a base.

The compounds according to the invention can be prepared, for example, as shown in the following reaction schemes:

Scheme 1

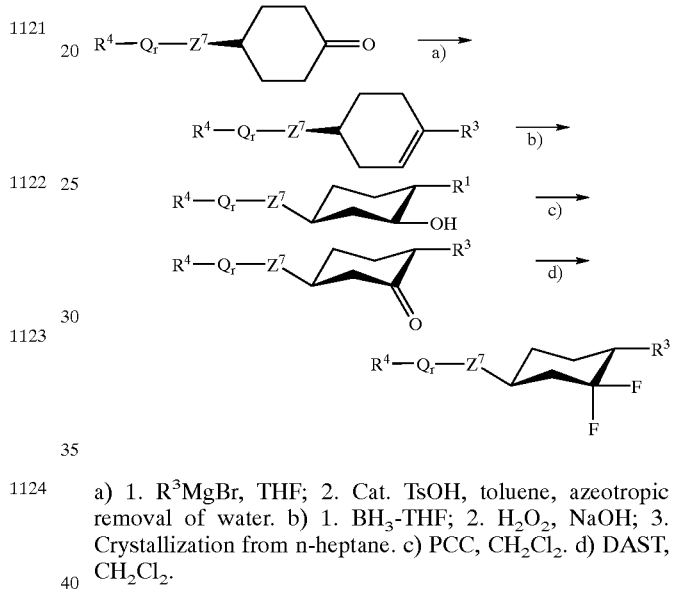

a) 1. $R^3$MgBr, THF; 2. Cat. TsOH, toluene, azeotropic removal of water. b) 1. $BH_3$-THF; 2. $H_2O_2$, NaOH; 3. Crystallization from n-heptane. c) PCC, $CH_2Cl_2$. d) DAST, $CH_2Cl_2$.

Scheme 2

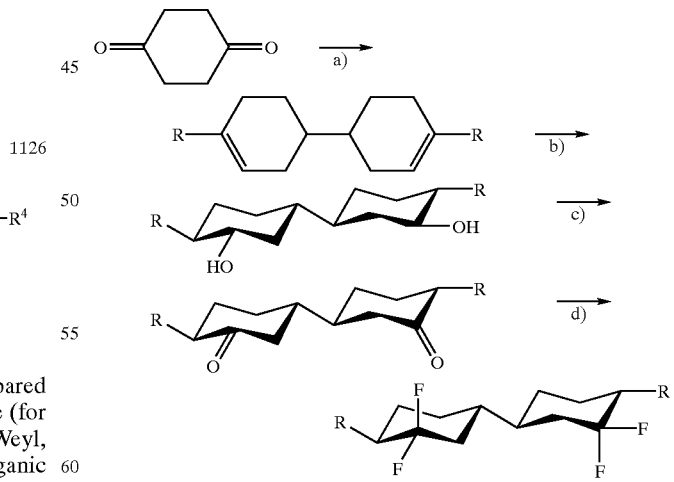

R=alkyl a) 1. RMgBr, THF; 2. Cat. TsOH, toluene, azeotropic removal of water. b) 1. $BH_3$-THF; 2. $H_2O_2$, NaOH; 3. Crystallization from n-heptane. c) PCC, $CH_2Cl_2$. d) DAST, $CH_2Cl_2$.

Scheme 3

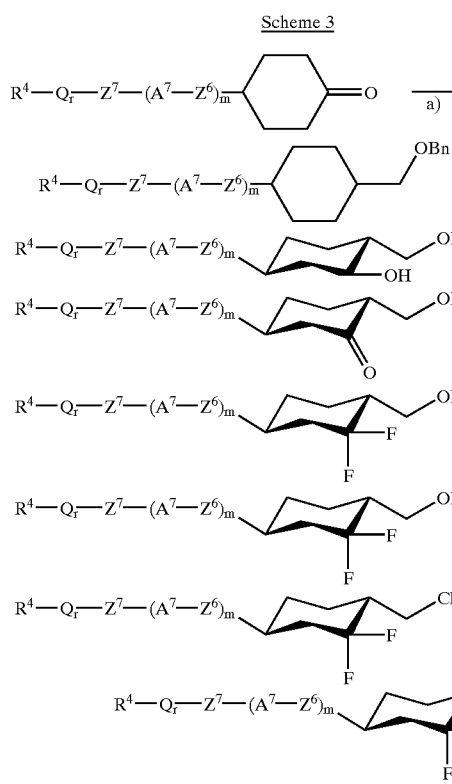

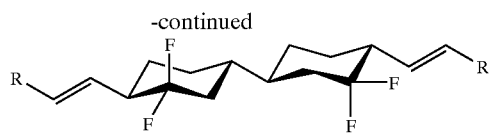

R=alkyl a) 1. BnOCH$_2$MgBr, THF; 2. Cat. TsOH, toluene, azeotropic removal of water. b) 1. BH$_3$-THF; 2. H$_2$O$_2$, NaOH; 3. Crystallization from n-heptane. c) PCC, CH$_2$Cl$_2$. d) DAST, CH$_2$Cl$_2$. e) H$_2$, 5% Pd/C. f) PCC, CH$_2$Cl$_2$. g) Ph$_3$P=CHR.

Scheme 5

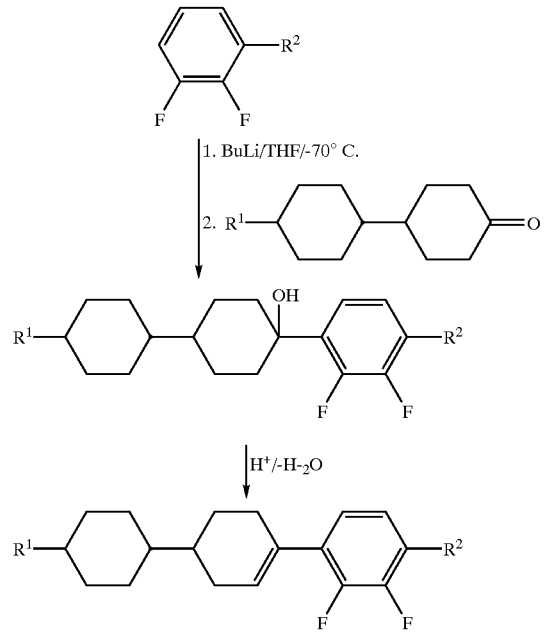

R=alkyl a) 1. BnOCH$_2$MgBr, THF; 2. Cat. TsOH, toluene, azeotropic removal of water. b) 1. BH$_3$-THF; 2. H$_2$O$_2$, NaOH; 3. Crystallization from n-heptane. C) PCC, CH$_2$Cl$_2$. d) DAST, CH$_2$Cl$_2$. e) H$_2$, 5% Pd/C. f) PCC, CH$_2$Cl$_2$. g) Ph$_3$P=CHR.

Scheme 4

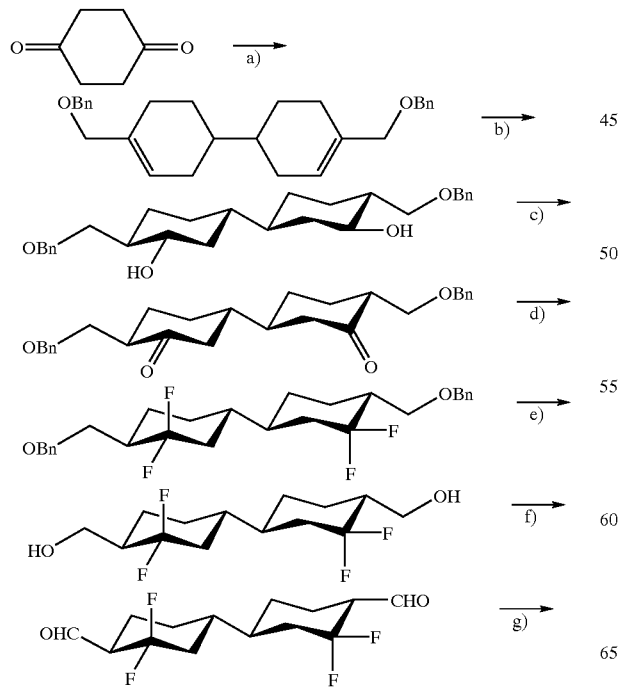

Scheme 6

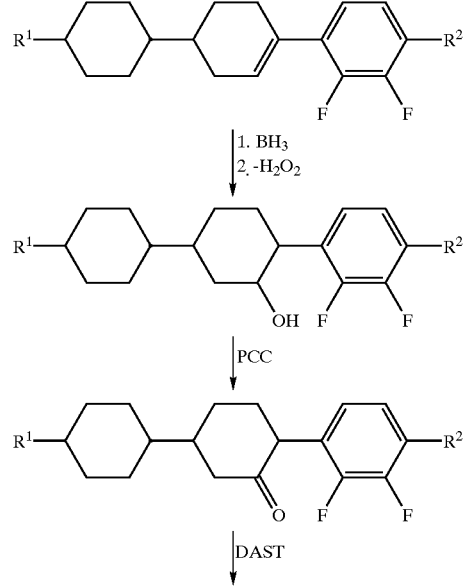

-continued

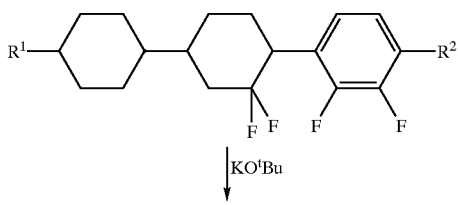

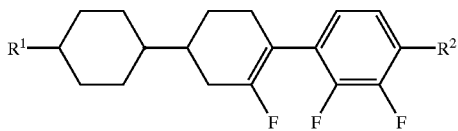

Scheme 7

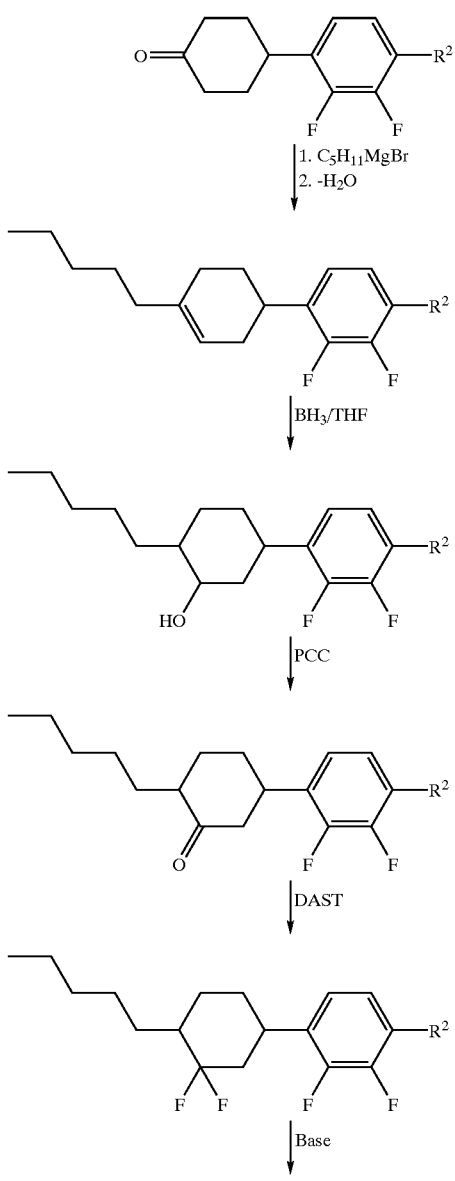

-continued

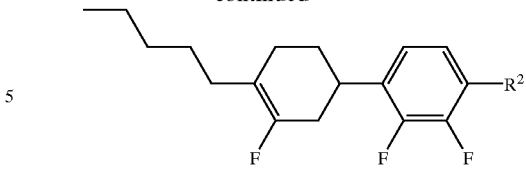

in which $R^1$, $R^2$, $R^3$ and $R^4$ are as defined above.

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

Suitable reactive derivatives of said carboxylic acids are in particular the acid halides, especially the chlorides and bromides, furthermore the anhydrides, azides or esters, in particular alkyl esters having 1–4 carbon atoms in the alkyl group.

Suitable reactive derivatives of said alcohols are in particular the corresponding metal alkoxides, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulphoxides, such as dimethyl sulphoxide or sulpholane. Water-immiscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol is generally carried out in the presence of a strong acid, for example a mineral acid, such as hydrochloric acid or sulphuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline-earth metal hydroxides, such as calcium hydroxide, or organic bases, such as triethylamine, pyridine, lutidine, collidine or quinoline. A further preferred embodiment of the esterification comprises first converting the alcohol into the sodium or potassium alkoxide, for example by treatment with ethanolic sodium hydroxide or potassium hydroxide solution, and isolating the product and reacting it with an acid anhydride or, in particular, acid chloride.

Nitriles can be obtained by replacement of halogens using copper cyanide or alkali metal cyanide.

Ethers of the formulae I, II and III are obtainable by etherification of corresponding hydroxyl compounds, the hydroxyl compound advantageously first being converted into a corresponding metal derivative, for example into the corresponding alkali metal alkoxide, by treatment with NaH, $NaNH_2$, NaOH, KOH, $Na_2CO_3$ or $K_2CO_3$. This metal derivative can then be reacted with the appropriate alkyl halide, alkyl sulphonate or dialkyl sulphate, advantageously in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° C. and 100° C.

The organometallic compounds are prepared, for example, by metal-halogen exchange (for example in accordance with Org. React. 6, 339–366 (1951)) between the corresponding halogen compound and an organolithium compound, such as, preferably, tert-butyllithium or lithium naphthalenide, or by reaction with magnesium turnings.

In addition, the compounds of the formulae I, II and III can be prepared by reducing a compound which contains one or more reducible groups and/or C—C bonds in place of H atoms, but otherwise conforms to the formulae I, II and III.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formulae I, II and III, but contain a cyclohexene ring or cyclohexanone ring in place of a cyclohexane ring and/or contain a —CH=CH— group in place of a —CH$_2$CH$_2$— group and/or contain a —CO— group in place of a —CH$_2$— group and/or contain a free or functionally derived (for example in the form of its p-toluenesulphonate) OH group in place of an H atom.

The reduction can be carried out, for example, by catalytic hydrogenation at temperatures between about 0° and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which may be employed in the form of oxides (for example $PtO_2$ or PdO), on a support (for example Pd on carbon, calcium carbonate or strontium carbonate) or in finely divided form.

Ketones can also be reduced by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.) to give the corresponding compounds of the formulae I, II and III which contain alkyl groups and/or —CH$_2$CH$_2$— bridges.

Furthermore, reductions using complex hydrides are possible. For example, arylsulphonyloxy groups can be removed reductively using LiAlH$_4$, in particular p-toluenesulphonyloxymethyl groups can be reduced to methyl groups, advantageously in an inert solvent, such as diethyl ether or THF, at temperatures between about 0 and 100° C.

Double bonds can be hydrogenated using NaBH$_4$ or tributyltin hydride in methanol.

The starting materials are either known or can be prepared analogously to known compounds.

The liquid-crystalline media according to the invention preferably comprise from 2 to 40 components, in particular from 4 to 30 components, as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylyl-ethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phr—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phr—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe-— and —G—Cyc—.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is called group B, R" is —F, —Cl, —NCS or —(O)$_i$CH$_{3-(k+1)}$F$_k$Cl$_1$, where i is 0 or 1, and k and 1 are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from Group A and/or Group B and/or Group C. The proportions by weight of the compounds from these groups in the media according to the invention are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5%–90% and in particular from 10% to 90%.

The media according to the invention preferably comprise from 1 to 40%, particularly preferably from 5 to 30%, of the compounds according to the invention. Preference is furthermore given to media which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, advantageously at elevated temperature. By means of suitable additives, the liquid-crystalline phases can be modified in accordance with the invention in such a manner that they can be used in all types of liquid-crystal display elements which have been disclosed hitherto. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the alignment of the nematic phases.

The entire disclosure of all applications, patents and publications, cited above and below, and of corresponding German Application 19914683.7, filed Mar. 31, 1999, Germany Patent Application No. 19914684.5, filed Mar. 31, 1999, and German Patent Application No. 19919435.1, filed Apr. 29, 1999, is hereby incorporated by reference.

EXAMPLES

The examples below are intended to illustrate the invention without representing a limitation. Above and below, percentages are percent by weight. All temperatures are given in degrees Celsius. m.p. denotes melting point, cl.p.= clearing point. Furthermore, C=crystalline state, N=nematic phase, Sm=smectic phase and I=isotropic phase. The numbers between these symbols indicate the conversion temperatures. Δn denotes the optical anisotropy (589 nm, 20° C.) and Δε the dielectric anisotropy (1 kHz, 20° C.).

The Δn and Δε values of the compounds according to the invention were obtained by extrapolation from liquid-crystalline mixtures consisting of 10% of the particular compound according to the invention and 90% of the commercially available liquid crystal ZLI 4792 (Merck, Darmstadt).

The viscosity (mm$^2$/sec) was determined at 20° C.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The following abbreviations are used:

| | |
|---|---|
| THF | tetrahydrofuran |
| KOtBu | potassium tert-butoxide |
| RT | room temperature |
| MTB ether | methyl tert-butyl ether |
| DAST | diethylaminosulphur trifluoride |
| TsOH | p-toluenesulphonic acid |
| PCC | pyridinium chlorochromate |

Example 1

1-(3,3-Difluoro-4-pentylcyclohexyl)-4-ethoxy-2,3-difluorobenzene a)

A solution of 54.5 ml of 1-bromopentane in 200 ml of THF was added dropwise to 10.7 g of magnesium turnings under a layer of 100 ml of THF, and the mixture was subsequently refluxed for 1 hour. A solution of 104.5 g of 4-(4-ethoxy-2,3-difluorophenyl)cyclohexanone (obtainable by lithiation of 4-ethoxy-2,3-difluorobenzene using n-butyllithium, reaction with 1,4-dioxaspiro[4.5]decan-8- one, dehydration and hydrogenation of the resultant alkene, followed by removal of the carbonyl protecting group under acidic conditions) in 500 ml of THF was then added dropwise at 40° C., and the mixture was refluxed for 2 hours. Conventional work-up gave 4-(4-ethoxy-2,3-difluorophenyl)-1-pentylcyclohexanol.

b)

A solution of 128.0 g of 4-(4-ethoxy-2,3-difluorophenyl)-1-pentylcyclohexanol in 1 l of toluene was refluxed in a water separator with addition of 5.0 g of toluene-4-sulphonic acid monohydrate. When all the water had been removed, the mixture was subjected to conventional work-up, giving 1-ethoxy-2,3-difluoro-4-(4-pentylcyclohex-3-enyl)benzene.

c)

53 g of 1-ethoxy-2,3-difluoro-4-(4-pentylcyclohex-3-enyl)benzene were dissolved in 500 ml of THF, and the mixture was cooled to 2° C. 195 ml of borane/THF complex were subsequently added dropwise over the course of 30 minutes with stirring. After the mixture had been stirred for a further 2 hours, 48 ml of ethanol were added dropwise to the solution at RT. Subsequently, firstly a solution of 10.6 g of sodium hydroxide and then 63 ml of 30% hydrogen peroxide were added dropwise. The mixture was subsequently refluxed for 2 hours and subjected to conventional work-up, giving 5-(4-ethoxy-2,3-difluorophenyl)-2-pentylcyclohexanol.

d)

48.2 g of 5-(4-ethoxy-2,3-difluorophenyl)-2-pentyl-cyclohexanol were dissolved in 600 ml of dichloromethane, and 30 g of Celite were added. 35.6 g of pyridinium chlorochromate were added with stirring, and the mixture was stirred at RT overnight. Conventional work-up gave 5-(4-ethoxy-2,3-difluorophenyl)-2-pentyl-cyclohexanone.

e)

10.0 g of 5-(4-ethoxy-2,3-difluorophenyl)-2-pentyl-cyclohexanone were dissolved in 100 ml of dichloromethane, and 10 ml of DAST were added dropwise at RT. After the mixture had been stirred overnight, it was poured into ice-water and subjected to conventional work-up, giving 1-(3,3-difluoro-4-pentylcyclohexyl)-4-ethoxy-2,3-difluorobenzene (C 92 I, $\Delta\epsilon$ –8.77, $\Delta$n 0.06).

The following compounds according to the invention are obtained analogously using the corresponding precursors:

Examples 2–13

| | $R^3$ | $(Z^6-A^7)_m$ | $R^4$ |
|---|---|---|---|
| (2) | n-Propyl | cyclohexyl | Vinyl ($\Delta\epsilon$ –4.7, $\Delta$n –0.011) |
| (3) | 1E-Pentenyl | cyclohexyl | 1E-Pentenyl |
| (4) | n-Propyl | —CH$_2$CH$_2$—cyclohexyl | n-Propyl |
| (5) | n-Pentyl | —CH$_2$CH$_2$—cyclohexyl | 1E-Propenyl |
| (6) | n-Propyl | difluorocyclohexyl | n-Pentyl (C 39 SmB 66 I, $\Delta\epsilon$ –1.9, $\Delta$n 0.010) |
| (7) | n-Propyl | —CH$_2$CH$_2$—difluorocyclohexyl | n-Propyl |

-continued
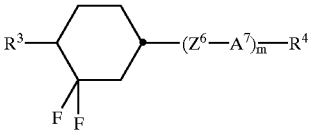
| R³ | (Z⁶—A⁷)ₘ | R⁴ |
|---|---|---|
| (8) n-Pentyl | 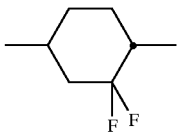 | n-Pentyl (C 73 SmB 91 I, Δε −1.8, Δn 0.022) |
| (9) Ethyl | 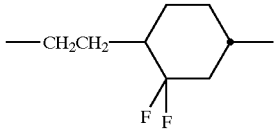 | n-Propyl |
| (10) n-Propyl | 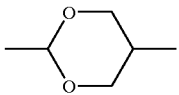 | 1E-Pentenyl |
| (11) n-Pentyl | 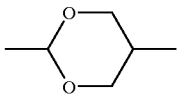 | n-Pentyl |
| (12) n-Pentyl | 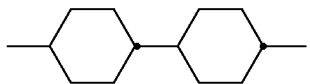 | n-Propyl |
| (13) Propyl | 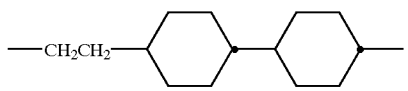 | Ethyl |
40
Examples 14–26
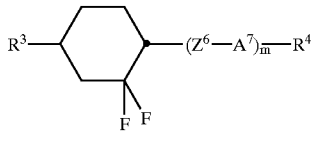
| R³ | (Z⁶—A⁷)ₘ | R⁴ |
|---|---|---|
| (14) n-Propyl |  | Vinyl (Δε −2.8, Δn 0.009) |
| (15) 1E-Pentenyl |  | n-Pentyl |
| (16) 1E-Pentenyl |  | 1E-Pentenyl |

-continued

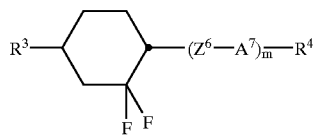

| | R³ | (Z⁶—A⁷)ₘ | R⁴ |
|---|---|---|---|
| (17) | n-Propyl | —CH₂CH₂—⟨cyclohexyl⟩— | n-Propyl |
| (18) | n-Pentyl | —CH₂CH₂—⟨cyclohexyl⟩— | 1E-Propenyl |
| (19) | n-Propyl | —⟨cyclohexyl-2,2-F₂⟩— | n-Pentyl |
| (20) | n-Propyl | —CH₂CH₂—⟨cyclohexyl-F₂⟩— | n-Propyl |
| (21) | n-Pentyl | —⟨cyclohexyl-F₂⟩— | n-Pentyl |
| (22) | Ethyl | —CH₂CH₂—⟨cyclohexyl-F₂⟩— | n-Propyl |
| (23) | n-Propyl | —⟨1,3-dioxane⟩— | 1E-Pentenyl |
| (24) | n-Pentyl | —⟨1,3-dioxane⟩— | n-Pentyl |
| (25) | n-Pentyl | —⟨cyclohexyl-cyclohexyl⟩— | n-Propyl |
| (26) | Propyl | —CH₂CH₂—⟨cyclohexyl-cyclohexyl⟩— | Ethyl |

Examples 27–39

| R³ | Z⁷—Q_r | R⁴ |
|---|---|---|
| (27) Pentyl | [2,3-difluoro-1,4-phenylene] | Methyl (Δε −5.70, Δn 0.038) |
| (28) 1E-Pentenyl | [phenyl-2,3-difluorophenylene] | n-Pentyloxy |
| (29) 1E-Pentenyl | [phenyl-CH₂CH₂-2,3-difluorophenylene] | 1E-Pentenyl |
| (30) n-Propyl | [2,3-difluoro-1,4-phenylene] | n-Propyloxy |
| (31) n-Pentyl | [2,2',3-trifluorobiphenylene] | 1E-Propenyl |
| (32) n-Propyl | [—CH₂CH₂—2,3-difluorophenylene] | n-Pentyl |
| (33) n-Propyl | [—CH₂CH₂—2,3-difluorophenylene] | n-Propyloxy |
| (34) n-Pentyl | [phenyl-2,3-difluorophenylene] | n-Pentyloxy |
| (35) Ethyl | [phenyl-2,3-difluorophenylene] | n-Propyl |

-continued

R³—[cyclohexane(F,F)]—Z⁷—Qr—R⁴

| R³ | Z⁷—Qr | R⁴ |
|---|---|---|
| (36) n-Propyl | —[phenyl]—CH₂CH₂—[phenyl(F,F)]— | 1E-Pentenyl |
| (37) n-Pentyl | —[phenyl(F,F)]— | n-Pentyl |
| (38) n-Pentyl | —CH₂CH₂—[phenyl(F,F)]— | n-Propyloxy |
| (39) Propyl | —CH₂CH₂—[phenyl]—[phenyl(F,F)]— | Ethyl |

Examples 40–52

R³—[cyclohexane(F,F)]—Z⁷—Qr—R⁴

| R⁴ | Z⁷—Qr | R⁴ |
|---|---|---|
| (40) 1E-Pentenyl | —[phenyl(F,F)]— | n-Propyl |
| (41) 1E-Pentenyl | —[phenyl]—[phenyl(F,F)]— | n-Pentyloxy |
| (42) 1E-Pentenyl | —[phenyl]—CH₂CH₂—[phenyl(F,F)]— | 1E-Pentenyl |

-continued
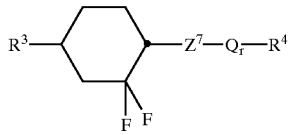
| R⁴ | Z⁷—Qᵣ | R⁴ |
|---|---|---|
| (43) n-Propyl | 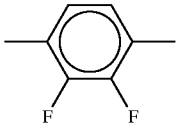 | n-Propyloxy |
| (44) n-Pentyl | 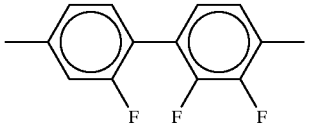 | 1E-Propenyl |
| (45) n-Propyl | 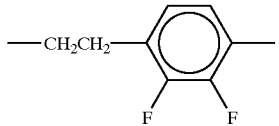 | n-Pentyl |
| (46) n-Propyl | 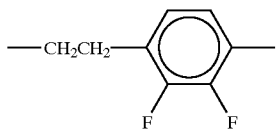 | n-Propyloxy |
| (47) n-Pentyl | 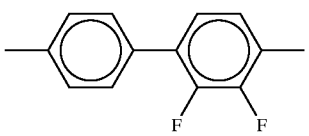 | n-Pentyloxy |
| (48) Ethyl | 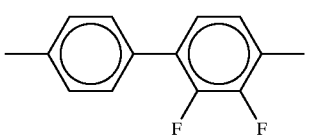 | n-Propyl |
| (49) n-Propyl | 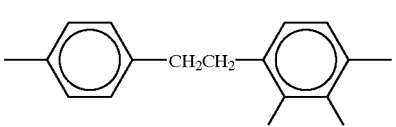 | 1E-Pentenyl |
| (50) n-Pentyl | 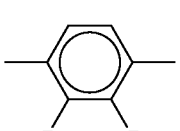 | n-Pentyl |
| (51) n-Pentyl | 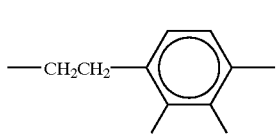 | n-Propyloxy |

-continued

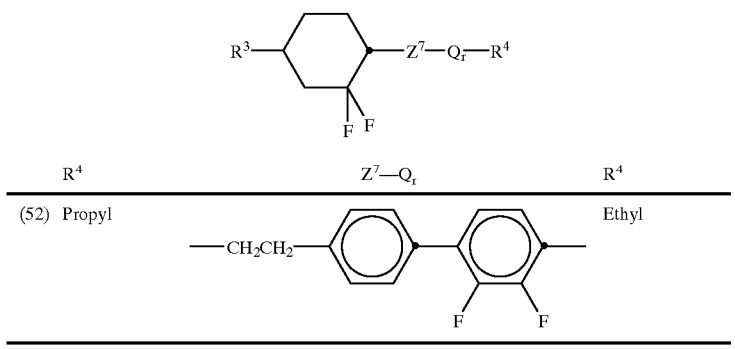

| R⁴ | Z⁷—Qᵣ | R⁴ |
|---|---|---|
| (52) Propyl | —CH₂CH₂— (biphenyl with 2F, 3F) | Ethyl |

Examples 53–65

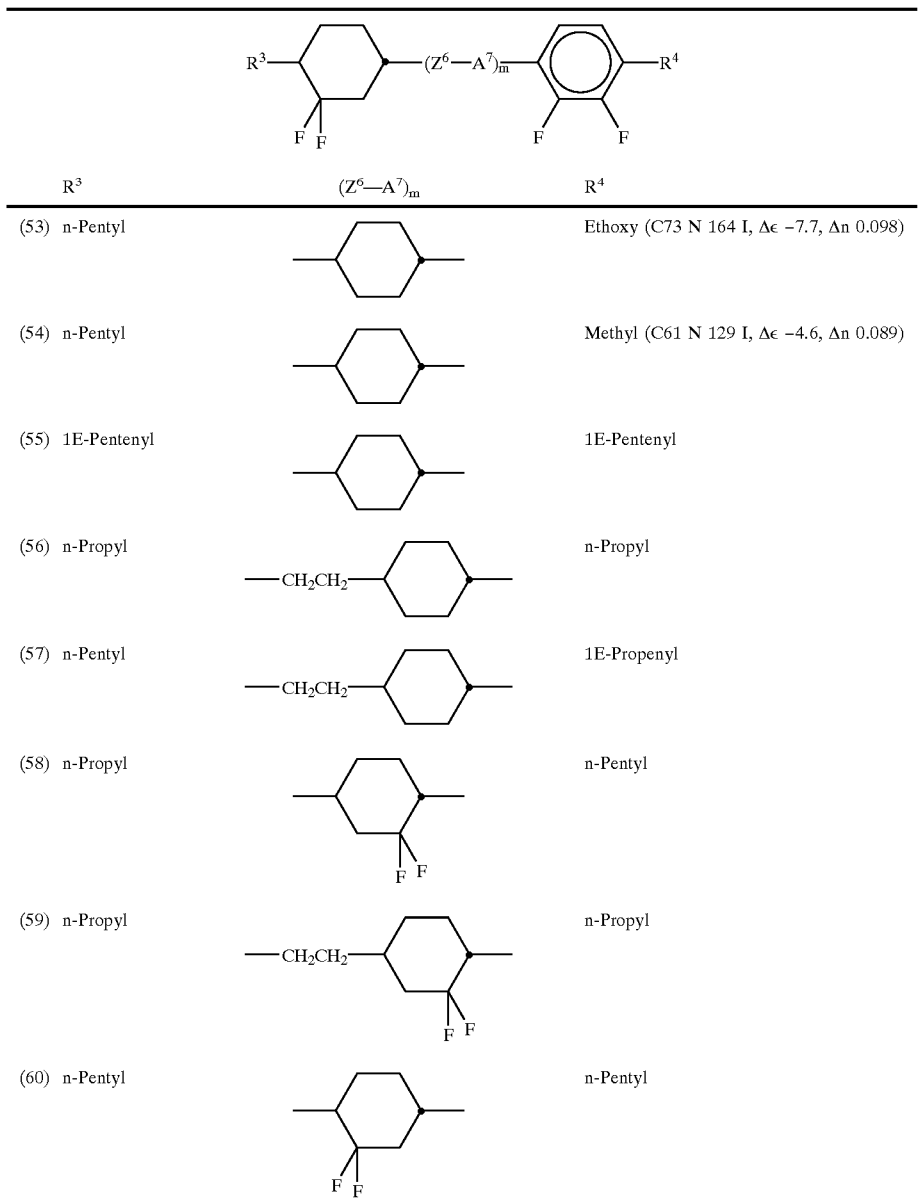

| R³ | (Z⁶—A⁷)ₘ | R⁴ |
|---|---|---|
| (53) n-Pentyl | cyclohexyl | Ethoxy (C73 N 164 I, Δε −7.7, Δn 0.098) |
| (54) n-Pentyl | cyclohexyl | Methyl (C61 N 129 I, Δε −4.6, Δn 0.089) |
| (55) 1E-Pentenyl | cyclohexyl | 1E-Pentenyl |
| (56) n-Propyl | —CH₂CH₂—cyclohexyl | n-Propyl |
| (57) n-Pentyl | —CH₂CH₂—cyclohexyl | 1E-Propenyl |
| (58) n-Propyl | cyclohexyl with F F | n-Pentyl |
| (59) n-Propyl | —CH₂CH₂—cyclohexyl with F F | n-Propyl |
| (60) n-Pentyl | cyclohexyl with F F | n-Pentyl |

-continued

R³—[cyclohexane(F,F)]—(Z⁶—A⁷)ₘ—[phenyl(F,F)]—R⁴

| R³ | (Z⁶—A⁷)ₘ | R⁴ |
| --- | --- | --- |
| (61) Ethyl | —CH₂CH₂—[cyclohexane(F,F)]— | n-Propyl |
| (62) n-Propyl | —[dioxane]— | 1E-Pentenyl |
| (63) n-Pentyl | —[dioxane]— | n-Pentyl |
| (64) n-Pentyl | —[cyclohexane-cyclohexane]— | n-Propyl |
| (65) Propyl | —CH₂CH₂—[cyclohexane-cyclohexane]— | Ethyl |

Examples 66–78

R³—[cyclohexane(F,F)]—(Z⁶—A⁷)ₘ—[phenyl(F,F)]—R⁴

| R³ | (Z⁶—A⁷)ₘ | R⁴ |
| --- | --- | --- |
| (66) 1E-Pentenyl | —[cyclohexane]— | n-Propyl |
| (67) 1E-Pentenyl | —[cyclohexane]— | n-Pentyl |
| (68) 1E-Pentenyl | —[cyclohexane]— | 1E-Pentenyl |
| (69) n-Propyl | —CH₂CH₂—[cyclohexane]— | n-Propyl |

-continued

R³—[cyclohexyl(2,2-F,F)]—(Z⁶—A⁷)ₘ—[phenyl(3,4-F,F)]—R⁴

| R³ | (Z⁶—A⁷)ₘ | R⁴ |
|---|---|---|
| (70) n-Pentyl | —CH₂CH₂—[cyclohexyl]— | 1E-Propenyl |
| (71) n-Propyl | —[cyclohexyl(F,F)]— | n-Pentyl |
| (72) n-Propyl | —CH₂CH₂—[cyclohexyl(F,F)]— | n-Propyl |
| (73) n-Pentyl | —[cyclohexyl(F,F)]— | n-Pentyl |
| (74) Ethyl | —CH₂CH₂—[cyclohexyl(F,F)]— | n-Propyl |
| (75) n-Propyl | —[1,3-dioxane]— | 1E-Pentenyl |
| (76) n-Pentyl | —[1,3-dioxane]— | n-Pentyl |
| (77) n-Pentyl | —[cyclohexyl]—[cyclohexyl]— | n-Propyl |
| (78) Propyl | —CH₂CH₂—[cyclohexyl]—[cyclohexyl]— | Ethyl |

Example 79

1-Ethoxy-2,3-difluoro-4-(3-fluoro-4-pentylcyclohex-3-enyl)benzene a)

A solution of 54.5 ml of 1-bromopentane in 200 ml of THF was added dropwise to 10.7 g of magnesium turnings under a layer of 100 ml of THF, and the mixture was subsequently refluxed for 1 hour. A solution of 104.5 g of 4-(4-ethoxy-2,3-difluorophenyl)cyclohexanone (obtainable by lithiation of 4-ethoxy-2,3-difluorobenzene using n-butyllithium, reaction with 1,4-dioxaspiro[4.5]decan-8-one, dehydration and hydrogenation of the resultant alkene, followed by removal of the carbonyl protecting group under acidic conditions) in 500 ml of THF was then added dropwise at 40° C., and the mixture was refluxed for 2 hours. Conventional work-up gave 4-(4-ethoxy-2,3-difluorophenyl)-1-pentylcyclohexanol.

b)

A solution of 128.0 g of 4-(4-ethoxy-2,3-difluorophenyl)-1-pentylcyclohexanol in 1 l of toluene was refluxed in a water separator with addition of 5.0 g of toluene-4-sulphonic acid monohydrate. When all the water had been removed, the mixture was subjected to conventional work-up, giving 1-ethoxy-2,3-difluoro-4-(4-pentylcyclohex-3-enyl)benzene.

c)

53 g of 1-ethoxy-2,3-difluoro-4-(4-pentylcyclohex-3-enyl)benzene were dissolved in 500 ml of THF, and the mixture was cooled to 2° C. 195 ml of borane/THF complex were subsequently added dropwise over the course of 30 minutes with stirring. After the mixture had been stirred for a further 2 hours, 48 ml of ethanol were added dropwise to the solution at RT. Subsequently, firstly a solution of 10.6 g of sodium hydroxide and then 63 ml of 30% hydrogen peroxide were added dropwise. The mixture was subsequently refluxed for 2 hours and subjected to conventional work-up, giving 5-(4-ethoxy-2,3-difluorophenyl)-2-pentylcyclohexanol.

d)

48.2 g of 5-(4-ethoxy-2,3-difluorophenyl)-2-pentyl-cyclohexanol were dissolved in 600 ml of dichloromethane, and 30 g of Celite were added. 35.6 g of pyridinium chlorochromate were added with stirring, and the mixture was stirred at RT overnight. Conventional work-up gave 5-(4-ethoxy-2,3-difluorophenyl)-2-pentyl-cyclohexanone.

e)

10.0 g of 5-(4-ethoxy-2,3-difluorophenyl)-2-pentyl-cyclohexanone were dissolved in 100 ml of dichloromethane, and 10 ml of DAST were added dropwise at RT. After the mixture had been stirred overnight, it was poured into ice-water and subjected to conventional work-up, giving a mixture of 1-(3,3-difluoro-4-pentylcyclohexyl)-4-ethoxy-2,3-difluorobenzene and 1-ethoxy-2,3-difluoro-4-(3-fluoro-4-pentylcyclohex-3-enyl)benzene, which was separated by chromatography.

f)

13.3 mol of diisopropylamine were added dropwise at 20° C. to 13.5 mol of n-butyllithium (15% in n-hexane) in 10 ml of THF. The solution was subsequently stirred for 10 minutes and added dropwise to a mixture consisting of 10 ml of THF and 13.5 mol of 1-(3,3-difluoro-4-pentylcyclohexyl)-4-ethoxy-2,3-difluorobenzene under a protective gas at −40° C. The reaction mixture was firstly stirred at −40° C. for 30 minutes and then at RT overnight.

Conventional work-up gave 1-ethoxy-2,3-difluoro-4-(3-fluoro-4-pentylcyclohex-3-enyl)benzene.

Example 80

4-(4-Ethoxy-2,3-difluorophenyl)-3-fluoro-4'-pentylbicyclohexyl-3-ene a)

45.0 g of 4-(4-ethoxy-2,3-difluorophenyl)-4'-pentylbicyclohexyl-3-ene (obtainable by lithiation of 4-ethoxy-2,3-difluorobenzene using n-butyllithium, reaction with 4'-pentylbicyclohexyl-4-one, followed by dehydration) were dissolved in 500 ml of THF, and the mixture was cooled to 2° C. 130 ml of borane/THF complex were subsequently added dropwise over the course of 30 minutes with stirring. After the mixture had been stirred for a further 2 hours, 32 ml of ethanol were added dropwise to the solution at RT. Subsequently, firstly a solution of 7.1 g of sodium hydroxide in 30 ml of water and then 42 ml of 30% hydrogen peroxide were added dropwise. The mixture was then refluxed for a further 2 hours and subjected to conventional work-up, giving 4-(4-ethoxy-2,3-difluorophenyl)-4'-pentylbicyclohexyl-3-ol.

b)

46.7 g of 4-(4-ethoxy-2,3-difluorophenyl)-4'-pentylbicyclohexyl-3-ol were dissolved in 600 ml of dichloromethane, and 20 g of Celite were added. 28.0 g of pyridinium chlorochromate were added with stirring, and the mixture was stirred overnight at RT. After 10 ml of 2-propanol had been added, the mixture was stirred for 1 hour and then subjected to conventional work-up, giving 4-(4-ethoxy-2,3-difluorophenyl)-4'-pentylbicyclohexyl-3-one.

c)

11.0 g of 4-(4-ethoxy-2,3-difluorophenyl)-4'-pentylbicyclohexyl-3-one were dissolved in 100 ml of dichloromethane, and 8 ml of DAST were added dropwise at RT. After the mixture had been stirred overnight, it was poured into ice-water and subjected to conventional work-up, giving a mixture of 4-(4-ethoxy-2,3-difluorophenyl)-3,3-difluoro-4'-pentylbicyclohexyl and 4-(4-ethoxy-2,3-difluorophenyl)-3-fluoro-4'-pentylbicyclohexyl-3-ene, which was separated by chromatography.

d)

13.3 mol of diisopropylamine were added dropwise at −20° C. to 13.5 mol of n-butyllithium (15% in n-hexane) in 10 ml of THF. The solution was subsequently stirred for 10 minutes and added dropwise to a mixture consisting of 10 ml of THF and 13.5 mol of 4-(4-ethoxy-2,3-difluorophenyl)-3,3-difluoro-4'-pentylbicyclohexyl under a protective gas at −40° C. The reaction mixture was firstly stirred at −40° C. for 30 minutes and then at RT overnight. Conventional work-up gave 4-(4-ethoxy-2,3-difluorophenyl)-3-fluoro-4'-pentylbicyclohexyl-3-ene. (C 78 N 148 I, Δε −4.77, Δn 0.116).

The following compounds according to the invention are obtained analogously using the corresponding precursors:

Examples 81–90

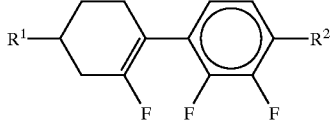

| | $R^1$ | $R^2$ |
|---|---|---|
| (81) | n-Pentyl | n-Propyl |
| (82) | n-Propyl | Ethoxy |
| (83) | n-Pentyl | n-Propyloxy |
| (84) | n-Propyl | Ethyl |
| (85) | n-Hexyl | n-Pentyloxy |
| (86) | n-Pentyl | Methyl |
| (87) | n-Propyl | n-Propyloxy |
| (88) | n-Pentyl | n-Butyl |
| (89) | n-Propyl | Methoxy |
| (90) | n-Pentyl | n-Pentyl |

Examples 91–101

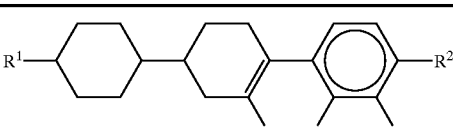

| | $R^1$ | $R^2$ |
|---|---|---|
| (91) | n-Pentyl | Ethoxy (C 78 N 148 I) |
| (92) | n-Propyl | Ethoxy (C 86 N 144 I, Δε −6.28, Δn 0.115) |

-continued

[Structure: R¹–cyclohexane–cyclohexene(F)–phenyl(F,F)–R²]

|  | R¹ | R² |
|---|---|---|
| (93) | n-Pentyl | Pentyloxy |
| (94) | n-Pentyl | n-Propyloxy |
| (95) | n-Propyl | Ethyl |
| (96) | n-Hexyl | n-Pentyloxy |
| (97) | n-Pentyl | Methyl |
| (98) | n-Propyl | n-Propyloxy |
| (99) | n-Pentyl | n-Butyl |
| (100) | n-Propyl | Methoxy |
| (101) | n-Pentyl | n-Pentyl |

Examples 102–112

[Structure: R¹–cyclohexane–CH₂CH₂–cyclohexene(F)–phenyl(F,F)–R²]

|  | R¹ | R² |
|---|---|---|
| (102) | n-Pentyloxy | Ethoxy |
| (103) | n-Propyl | Ethoxy |
| (104) | n-Pentyl | Ethoxy |
| (105) | n-Pentyl | n-Propyloxy |
| (106) | n-Propyl | Ethyl |
| (107) | n-Hexyl | n-Pentyloxy |
| (108) | n-Pentyl | Methyl |
| (109) | n-Propyl | n-Propyloxy |
| (110) | n-Pentyl | n-Butyl |
| (111) | n-Propyl | Methoxy |
| (112) | n-Pentyl | n-Pentyl |

Examples 113–123

[Structure: R¹–cyclohexene(F)–phenyl–phenyl(F,F)–R²]

|  | R¹ | R² |
|---|---|---|
| (113) | n-Pentyloxy | Ethoxy |
| (114) | n-Propyl | Ethoxy |
| (115) | n-Pentyl | Ethoxy |
| (116) | n-Pentyl | n-Propyloxy |
| (117) | n-Propyl | Ethyl |
| (118) | n-Hexyl | n-Pentyloxy |
| (119) | n-Pentyl | Methyl |
| (120) | n-Propyl | n-Propyloxy |
| (121) | n-Pentyl | n-Butyl |
| (122) | n-Propyl | Methoxy |
| (123) | n-Pentyl | n-Pentyl |

Examples 124–134

[Structure: R¹–cyclohexene(F)–phenyl–CH₂CH₂–phenyl(F,F)–R²]

|  | R¹ | R² |
|---|---|---|
| (124) | n-Pentyloxy | Ethoxy |
| (125) | n-Propyl | Ethoxy |
| (126) | n-Pentyl | Ethoxy |
| (127) | n-Pentyl | n-Propyloxy |
| (128) | n-Propyl | Ethyl |
| (129) | n-Hexyl | n-Pentyloxy |
| (130) | n-Pentyl | Methyl |
| (131) | n-Propyl | n-Propyloxy |
| (132) | n-Pentyl | n-Butyl |
| (133) | n-Propyl | Methoxy |
| (134) | n-Pentyl | n-Pentyl |

Examples 135–145

[Structure: R¹–cyclohexene(F)–cyclohexane–phenyl(F,F)–R²]

|  | R¹ | R² |
|---|---|---|
| (135) | n-Pentyloxy | Ethoxy |
| (136) | n-Propyl | Ethoxy |
| (137) | n-Pentyl | Ethoxy |
| (138) | n-Pentyl | n-Propyloxy |
| (139) | n-Propyl | Ethyl |
| (140) | n-Hexyl | n-Pentyloxy |
| (141) | n-Pentyl | Methyl |
| (142) | n-Propyl | n-Propyloxy |
| (143) | n-Pentyl | n-Butyl |
| (144) | n-Propyl | Methoxy |
| (145) | n-Pentyl | n-Pentyl |

Examples 146–156

[Structure: R¹–cyclohexene(F)–phenyl–CH₂CH₂–cyclohexane–R²]

|  | R¹ | R² |
|---|---|---|
| (146) | n-Pentyloxy | Ethoxy |
| (147) | n-Propyl | Ethoxy |
| (148) | n-Pentyl | Ethoxy |
| (149) | n-Pentyl | n-Propyloxy |
| (150) | n-Propyl | Ethyl |
| (151) | n-Hexyl | n-Pentyloxy |
| (152) | n-Pentyl | Methyl |
| (153) | n-Propyl | n-Propyloxy |
| (154) | n-Pentyl | n-Butyl |
| (155) | n-Propyl | Methoxy |
| (156) | n-Pentyl | n-Pentyl |

Examples 157–167

R¹—[cyclohexene-F]—[phenyl-F,F]—R²

| R¹ | R² |
|---|---|
| (157) n-Pentyloxy | Ethoxy |
| (158) n-Propyl | Ethoxy |
| (159) n-Pentyl | Ethoxy |
| (160) n-Pentyl | n-Propyloxy |
| (161) n-Propyl | Ethyl |
| (162) n-Hexyl | n-Pentyloxy |
| (163) n-Pentyl | Methyl |
| (164) n-Propyl | n-Propyloxy |
| (165) n-Pentyl | n-Butyl |
| (166) n-Propyl | Methoxy |
| (167) n-Pentyl | n-Pentyl |

Examples 168–178

R¹—[cyclohexene-F]—[cyclohexyl]—[phenyl-F,F]—R²

| R¹ | R² |
|---|---|
| (168) n-Pentyloxy | Ethoxy |
| (169) n-Propyl | Ethoxy |
| (170) n-Pentyl | Ethoxy |
| (171) n-Pentyl | n-Propyloxy |
| (172) n-Propyl | Ethyl |
| (173) n-Hexyl | n-Pentyloxy |
| (174) n-Pentyl | Methyl |
| (175) n-Propyl | n-Propyloxy |
| (176) n-Pentyl | n-Butyl |
| (177) n-Propyl | Methoxy |
| (178) n-Pentyl | n-Pentyl |

Examples 179–189

R¹—[cyclohexyl]—[cyclohexene-F]—[phenyl-F,F]—R²

| R¹ | R² |
|---|---|
| (179) n-Pentyloxy | Ethoxy |
| (180) n-Propyl | Ethoxy |
| (181) n-Pentyl | Ethoxy |
| (182) n-Pentyl | n-Propyloxy |
| (183) n-Propyl | Ethyl |
| (184) n-Hexyl | n-Pentyloxy |
| (185) n-Pentyl | Methyl |
| (186) n-Propyl | n-Propyloxy |
| (187) n-Pentyl | n-Butyl |
| (188) n-Propyl | Methoxy |
| (189) n-Pentyl | n-Pentyl |

Examples 190–200

R¹—[cyclohexene-F]—[phenyl-F]—[phenyl-F]—R²

| R¹ | R² |
|---|---|
| (190) n-Pentyloxy | Ethoxy |
| (191) n-Propyl | Ethoxy |
| (192) n-Pentyl | Ethoxy |
| (193) n-Pentyl | n-Propyloxy |
| (194) n-Propyl | Ethyl |
| (195) n-Hexyl | n-Pentyloxy |
| (196) n-Pentyl | Methyl |
| (197) n-Propyl | n-Propyloxy |
| (198) n-Pentyl | n-Butyl |
| (199) n-Propyl | Methoxy |
| (200) n-Pentyl | n-Pentyl |

Examples 201–211

R¹—[cyclohexene-F]—[cyclohexene-F]—[phenyl-F,F]—R²

| R¹ | R² |
|---|---|
| (201) n-Pentyloxy | Ethoxy |
| (202) n-Propyl | Ethoxy |
| (203) n-Pentyl | Ethoxy |
| (204) n-Pentyl | n-Propyloxy |
| (205) n-Propyl | Ethyl |
| (206) n-Hexyl | n-Pentyloxy |
| (207) n-Pentyl | Methyl |
| (208) n-Propyl | n-Propyloxy |
| (209) n-Pentyl | n-Butyl |
| (210) n-Propyl | Methoxy |
| (211) n-Pentyl | n-Pentyl |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A fluorocyclohexene compound of formula I

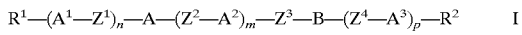

wherein

R¹ and R², independently of one another, are each H, —CN, —F, —OCHF$_2$, —OCF$_3$, —OCHFCF$_3$, —OCH$_2$CF$_3$ or —OCF$_2$CF$_3$, alkyl having 1–12 carbon atoms which is unsubstituted or at least monosubstituted by halogen or CN, wherein one or more CH$_2$ groups of the alkyl groups may in each case, independently of one another, be replaced by —O—, —S—, —CO—,

,

—CO—O—, —O—CO—, —O—CO—O— or —CH=CH— in such a way that heteroatoms are not connected directly;

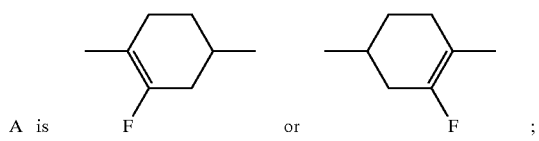

A is

A¹, A² and A³ are in each case independently of one another,
a) a trans-1,4-cyclohexylene wherein one or more non adjacent CH₂ groups may in each case, independently of one another, be replaced by —O—or —S—,
b) a 1,4-phenylene wherein one or two CH groups may in each case, independently of one another, be replaced by N, and which is unsubstituted or substituted by CN, Cl or F,
c) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl,
d) 1,4-cyclohexenylene,

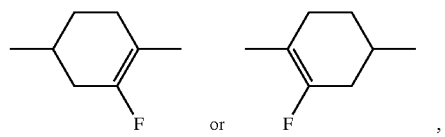

B, is

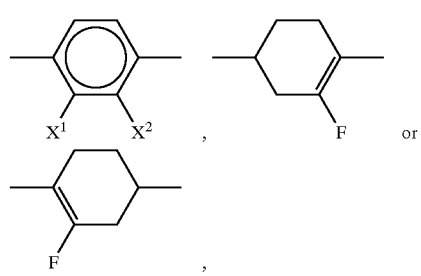

B can also be trans-1,4-cyclohexylene, in which one or more non-adjacent CH₂ groups may in each case, independently of one another, be replaced by —O—or —S—, when -n is 0 and Z³ is not a single bond, -n is 1 and Z¹ is not a single bond, or -n is 1 and A¹ has a meaning according to a), c) or d);

X¹ and X², independently of one another, are each F, Cl, CN, CF₃ or CHF₂;

Z¹, Z², Z³ and Z⁴ are each, independently of one another, —CO—O—, —O—CO—, —CH₂O—, —O—, —O—CH₂—, —CH₂CH₂—, —CH=CH—, —C≡C—, —CF₂CF₂—, —OCF₂—, —CF₂O—, —CH=CF—, —CF=CH— or a single bond;

n, m and p, independently of one another, are each 0, 1, 2 or 3; and m+n+p is 0, 1, 2 or 3.

2. A fluorocyclohexene according to claim 1, wherein R¹ and R², independently of one another, are each straight-chain alkyl having 1 to 10 carbon atoms, alkoxy having 1 to 10 carbon atoms, alkenyl having 2 to 10 carbon atoms, or alkenyloxy having 2 to 10 carbon atoms.

3. A fluorocyclohexene according to claim 1, wherein m and n are each 0 or 1.

4. A fluorocyclohexene according to claim 1, wherein p is 0.

5. A fluorocyclohexene according to claim 1, wherein Z¹, Z², Z³ and Z⁴ are each independently of one another, —CH₂CH₂—, —COO—, —OOC— or a single bond.

6. A fluorocyclohexene according to claim 1, wherein X¹ and X² are simultaneously F.

7. A fluorocyclohexene according to claim 1, wherein:
R¹ and R², independently of one another, are each straight-chain alkyl having 1 to 10 carbon atoms, alkoxy having 1 to 10 carbon atoms, alkenyl having 2 to 10 carbon atoms, or alkenyloxy having 2 to 10 carbon atoms;
m and n are each 0 or 1;
p is 0;
Z¹, Z², Z³ and Z⁴ are each independently of one another, —CH₂CH₂—, —COO—, —OOC— or a single bond; and
X¹ and X² are simultaneously F.

8. A fluorocyclohexene compound according to claim 1, wherein said compound is of formula IA:

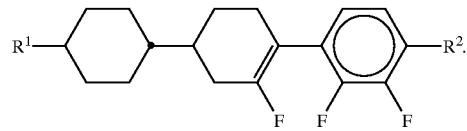

9. A difluorocyclohexane compound of formula III

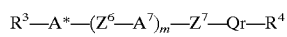

wherein

R³ and R⁴, independently of one another, are each H, alkyl having 1–12 carbon atoms, or alkyl having 1–12 carbon atoms in which one or more CH₂ groups are each, independently of one another, replaced by —O—or —CH=CH— in such a way that heteroatoms are not connected directly;

A* is

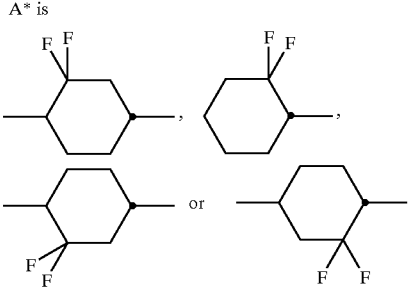

A⁷ is in each case, independently of one another, trans-1,4-cyclohexylene radical, wherein one or more non-adjacent CH₂ groups may in each case, independently, be replaced by —O—or —S—, and where the radical may be monosubstituted by Cl or F, Q is

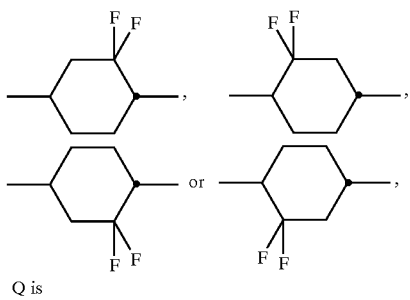

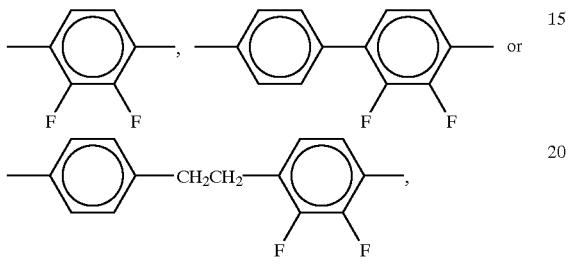

$Z^6$ and $Z^7$ are each, independently of one another, —CO—O—, —O—CO—, —CH$_2$O—, —O—, —O—CH$_2$—, —CH$_2$CH$_2$—, —CH═CH—, —C≡C—, —CF$_2$CF$_2$—, —OCF$_2$, —CF$_2$O—, —CH$_2$CF$_2$—, —CF$_2$CH$_2$— or a single bond;

m is 0, 1, 2 or 3;
r is 0 or 1; and
m+r is 1, 2 or 3;
with the proviso that compounds in which
m is 1,
r is 0,
$Z^6$ is a single bond,
$A^7$ is cyclohexane-1,4-diyl and
$R^3$ and $R^4$ are alkyl, or alkyl in which, one CH$_2$ group is replaced by —O—,
are excluded.

10. A difluorocyclohexane according to claim 9, wherein $R^3$ and $R^4$, independently of one another, are each straight-chain alkyl or alkoxy having 1 to 10 carbon atoms, alkenyl having 2 to 10 carbon atoms, or alkenyloxy having 2 to 10 carbon atoms.

11. A difluorocyclohexane according to claim 9, wherein m is 0, 1 or 2.

12. A difluorocyclohexane according to claim 9, wherein $Z^6$ and $Z^7$, independently of one another, are each —CH$_2$CH$_2$—, —COO—, —OOC— or a single bond.

13. A difluorocyclohexane according to claim 9, wherein
$R^3$ and $R^4$, independently of one another, are each straight-chain alkyl or alkoxy having 1 to 10 carbon atoms, alkenyl having 2 to 10 carbon atoms, or alkenyloxy having 2 to 10 carbon atoms;
m is 0, 1 or 2; and
$Z^6$ and $Z^7$, independently of one another, are —CH$_2$CH$_2$—, —COO—, —OOC— or a single bond.

14. In a liquid crystal medium comprising two or more liquid crystal compounds, the improvement wherein said medium contains at least one compound according to claim 1.

15. In a liquid crystal medium comprising two or more liquid crystal compounds, the improvement wherein said medium contains at least one compound according to claim 9.

16. A liquid-crystalline medium according to claim 14, wherein said medium further contains at least one compound of formula III

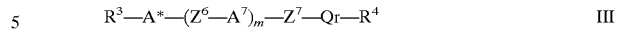

$$R^3—A*—(Z^6—A^7)_m—Z^7—Qr—R^4 \quad\quad III$$

wherein
$R^3$ and $R^4$, independently of one another, are each H, alkyl having 1–12 carbon atoms, or alkyl having 1–12 carbon atoms in which one or more CH$_2$ groups are each, independently of one another, replaced by —O— or —CH═CH— in such a way that heteroatoms are not connected directly;

A* is

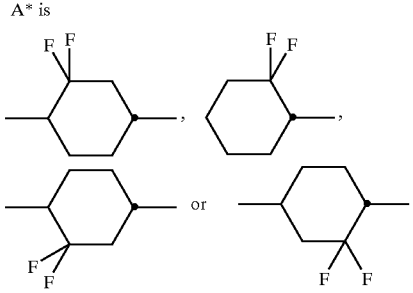

$A^7$ is in each case, independently of one another, trans-1,4-cyclohexylene radical, wherein one or more non-adjacent CH$_2$ groups may in each case, independently, be replaced by —O— or —S—, and where the radical may be monosubstituted by Cl or F,

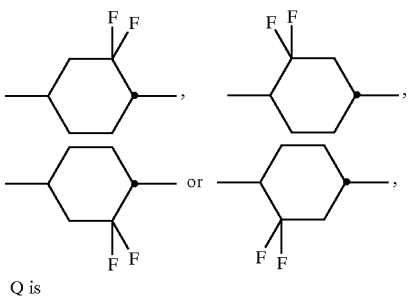

Q is

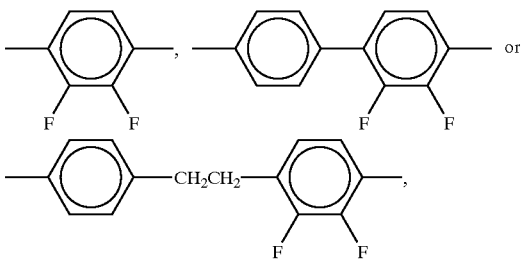

$Z^6$ and $Z^7$ are each, independently of one another, —CO—O—, —O—CO—, —CH$_2$O—, —O—, —O—CH$_2$—, —CH$_2$CH$_2$—, —CH═CH—, —C≡C—, —CF$_2$CF$_2$—, —OCF$_2$, —CF$_2$O—, —CH$_2$CF$_2$—, —CF$_2$CH$_2$— or a single bond;

m is 0, 1, 2 or 3;
r is 0 or 1; and
m+r is 1, 2 or 3;
with the proviso that compounds in which
m is 1, r is 0, $Z^6$ is a single bond, $A^7$ is cyclohexane-1,4-diyl and $R^3$ and $R^4$ are alkyl, or alkyl in which, one $CH_2$ group is replaced by —O—, are excluded.

17. In a liquid-crystal display element containing a liquid-crystalline medium, the improvement wherein said medium is a medium according to claim 14.

18. In a liquid-crystal display element containing a liquid-crystalline medium, the improvement wherein said medium is a medium according to claim 15.

19. In a liquid-crystal display element containing a liquid-crystalline medium, the improvement wherein said medium is a medium according to claim 16.

20. In an electro-optical display element containing a dielectric, the improvement wherein said dielectric is a liquid-crystalline medium according to claim 14.

21. In an electro-optical display element containing a dielectric, the improvement wherein said dielectric is a liquid-crystalline medium according to claim 15.

22. In an electro-optical display element containing a dielectric, the improvement wherein said dielectric is a liquid-crystalline medium according to claim 16.

23. A compound according to claim 1, wherein B is

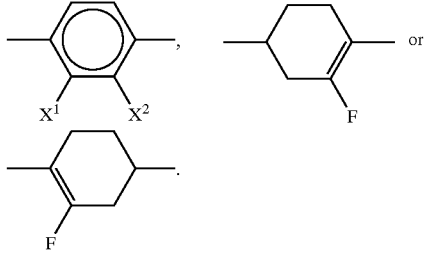

24. A fluorocyclohexene compound of formula I

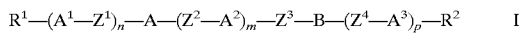   I wherein $R^1$ and $R^2$, independently of one another, are each H, —CN, —F, —OCHF$_2$, —OCF$_3$, —OCHFCF$_3$, —OCH$_2$CF$_3$ or —OCF$_2$CF$_3$, alkyl having 1–12 carbon atoms which is unsubstituted or at least monosubstituted by halogen or CN, wherein one or more $CH_2$ groups of the alkyl groups may in each case, independently of one another, be replaced by —O—, —S—, —CO—,

—CO—O—, —O—CO—, —O—CO—O— or —CH=CH— in such a way that heteroatoms are not connected directly;

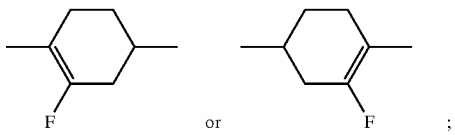

A is $A^1$, $A^2$ and $A^3$ are in each case independently of one another,
   a) a trans-1,4-cyclohexylene wherein one or more non-adjacent $CH_2$ groups may in each case, independently of one another, be replaced by —O—or —S—,
   b) a 1,4-phenylene wherein one or two CH groups may in each case, independently of one another, be replaced by N, and which is unsubstituted or substituted by CN, Cl or F,
   c) 1,4-bicyclo[2.2.2]octylene, piperidine-1,4-diyl, naphthalene-2,6-diyl, decahydronaphthalene-2,6-diyl, or 1,2,3,4-tetrahydronaphthalene-2,6-diyl,
   d) 1,4-cyclohexenylene,

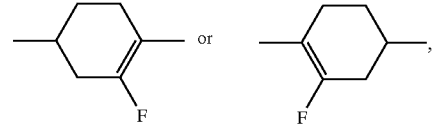

B, is trans-1,4-cyclohexylene, in which one or more non-adjacent $CH_2$ groups may in each case, independently of one another, be replaced by —O— or —S—,

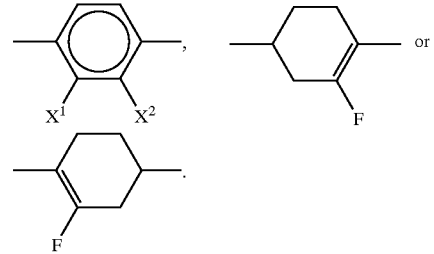

$X^1$ and $X^2$, independently of one another, are each F, Cl, CN, $CF_3$ or $CHF_2$;

$Z^1$, $Z^2$, and $Z^4$ are each, independently of one another, —CO—O—, —O—CO—, —CH$_2$O—, —O—, —O—CH$_2$—, —CH$_2$CH$_2$—, —CH=CH—, —C≡C—, —CF$_2$CF$_2$—, —OCF$_2$—, —CF$_2$O—, —CH=CF—, —CF=CH— or a single bond;

$Z^3$ is —CO—O—, —O—CO—, —CH$_2$O—, —O—, —O—CH$_2$—, —CH$_2$CH$_2$—, —CH=CH—, —C≡C—, —CF$_2$CF$_2$—, —OCF$_2$—, —CF$_2$O—, —CH=CF—, or —CF=CH—;

n is 0;

m is 0, 1, 2, or 3;

p is 0, 1, 2, or 3; and m+n+p is 0, 1, 2 or 3.

* * * * *

UNITED STATES PATENT AND TRADEMARK OFFICE
CERTIFICATE OF CORRECTION

| | | |
|---|---|---|
| PATENT NO. | : 6,475,595 B1 | |
| APPLICATION NO. | : 09/540882 | |
| DATED | : November 5, 2002 | |
| INVENTOR(S) | : Matthias Bremer | |

It is certified that error appears in the above-identified patent and that said Letters Patent is hereby corrected as shown below:

Column 53, line 38, reads "B, is" should read --B is--
Column 53, line 52, reads "-O-or" should read -- -O- or--
Column 53, lines 53-54, begin a new line at each -- -n--
Column 54, line 46, reads "-O-or" should read -- -O- or--
Column 54, line 66, reads "-O-or" should read -- -O- or--
Column 55, line 39, reads "in which, one" should read --in which one--
Column 56, line 22, insert comma following definition for A*
Column 57, line 3, reads "$A^7$is" should read --$A^7$ is--
Column 57, line 3, reads "diyl and" should read --diyl, and--
Column 57, line 4, reads "in which, one" should read --in which one--
Column 58, line 8, move "A is" to line 1
Column 58, line 30, reads "B, is" should read --B is--
Column 58, line 32, reads "-O-or" should read -- -O- or--
Column 58, line 40, replace period with comma at the end of definition for B Signed and Sealed this Eighteenth Day of November, 2008

JON W. DUDAS
*Director of the United States Patent and Trademark Office*